United States Patent
Achan

(10) Patent No.: US 8,000,977 B2
(45) Date of Patent: Aug. 16, 2011

(54) SYSTEM AND METHOD TO DEVELOP HEALTH-CARE INFORMATION SYSTEMS

(75) Inventor: Pradeep Padmakshan Achan, Castro Valley, CA (US)

(73) Assignee: Healthcare Charities, Inc., Castro Valley, CA (US)

( * ) Notice: Subject to any disclaimer, the term of this patent is extended or adjusted under 35 U.S.C. 154(b) by 2067 days.

(21) Appl. No.: 10/799,042

(22) Filed: Mar. 11, 2004

(65) Prior Publication Data

US 2005/0203771 A1 Sep. 15, 2005

(51) Int. Cl.
 - G06F 7/00 (2006.01)
 - G06F 17/00 (2006.01)
 - G06F 9/44 (2006.01)

(52) U.S. Cl. .................... 705/2; 705/3; 717/106

(58) Field of Classification Search ............ 705/2, 3; 717/106

See application file for complete search history.

(56) References Cited

U.S. PATENT DOCUMENTS

| | | | | |
|---|---|---|---|---|
| 6,742,015 | B1* | 5/2004 | Bowman-Amuah | 718/101 |
| 2003/0204415 | A1* | 10/2003 | Knowlton | 705/2 |
| 2005/0004814 | A1* | 1/2005 | Seltzer | 705/2 |

OTHER PUBLICATIONS

Murray et al.,"An Investigation of Specifications for Migrating to a Web Portal Framework for the Dissemination of Health Information within a Public Health Network" Proceedings of the 35th Hawaii International Conference on Systems Sciences—2002.*
IBM—"Web Services Conceptual Architecture (WSCA 1.0)" May 2001.*
Packeteer, "Enhancing MPLS Network Performance" Jul. 2004 (not prior art but for record only).*
Van Poppel editor, "HL7 Conformance Status Overview—Draft C" Oct. 14, 2003.*
Schramm et al., "Incremental HER introduction considering the situation in health care and the current standards under development" EM International congress Series 1230 (2001) pp. 889-894.*
Gawlick, Dieter "The Database as the application integration platform" as downloaded from research.microsoft.com on Apr. 6, 2011.*
Bakken, David, "Middleware" Washington State University Apr. 2004.*

* cited by examiner

Primary Examiner — Robert W Morgan
Assistant Examiner — Neal R Sereboff
(74) Attorney, Agent, or Firm — Donald R. Boys; Central Coast Patent Agency, Inc

(57) ABSTRACT

A method of and a system for development of health care information Systems (HIS) are disclosed. The method includes providing software programming interfaces for development of application modules, communication interfaces for establishing communication between various modules, and resource management interfaces for allocation of resources such as memory. The system comprises of a server with a health care middleware operating system (HMOS). The HMOS is designed as a multi-tier architecture with 3 tiers namely, application tier, domain services tier, and Foundations tier.

5 Claims, 16 Drawing Sheets

SYSTEM AND METHOD TO DEVELOP HEALTH-CARE INFORMATION SYSTEMS

FIELD OF THE INVENTION

Figure 1:
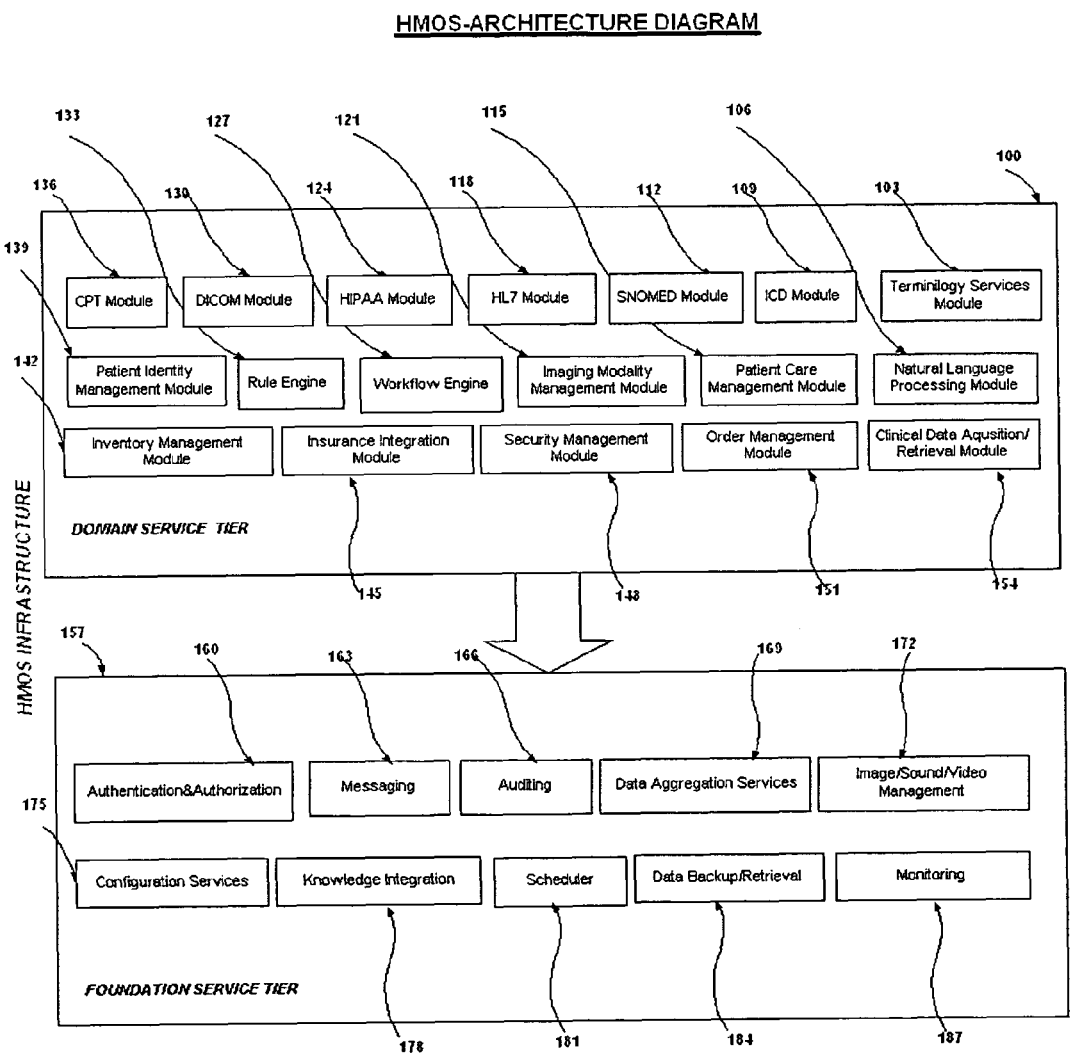

The present invention in the field of information technology has extensive applications in the health care domain and provides a framework for development of innovative health care information management systems.

BACKGROUND OF THE INVENTION

Delivery of life-critical health care requires timely access to mission-critical health care information. Health care delivery institutions the world over, whether in the public or private sectors, are faced with an uphill battle of ensuring people are protected by timely access to high quality health care at an affordable price.

Even sophisticated health care institutions in the advanced nations are plagued by lack of timely access to patient-records and related knowledge base, which are up to date and consistent across all domains such as clinical, biographic, financial etc. Empowered by a facility to accurately record and retrieve information on patient-care, medical personnel would be motivated to guarantee that a patient is receiving the best available treatment at a reasonable price. In addition to hygienically clean environment and life-style, a patient's welfare depends on availability of adequate supply of safe prescriptions, having minimal side effects.

Frequently, by a review of patient's information from the different sources referred to, diagnostic/therapeutic procedures prescribed by the medical team are often questionable or inappropriate, for the reasons noted hereunder:

Imprecise—usually doctor's notes are hand-written or scribbled. Nurses and pharmacists are very likely to misread the physician's instructions and are prone to take incorrect follow-up actions.

Contrasting—two or more physicians attending on a patient often independently prescribe medication for the same patient. If they fail to consult with each other, or when a patient's records are not available for timely reference by medical personnel before specifying the next course of treatment, this results in potentially life-threatening side effects. Even an alert nurse or pharmacist hardly ever catches such errors in a timely fashion.

Ill-timed—Some prescribed tests/procedures frequently need to be scheduled at the proper time and carried out in a specific order. Problems are often reported when the tests are not well coordinated. As a minimum, two items need to be addressed: (1) record of the required tests and procedures to be performed and their schedule and, (2) a list of equipment and services along with their availability. When the vital elements of information are in different and/or incompatible information systems, matching these lists to prescribe an appropriate treatment program is very difficult. It is conceivable that a patient could be scheduled for a test when the appropriate gear or medical personnel with relevant expertise are unavailable, leading to disastrous results depending on the severity of the patient's medical condition.

Currently available health care information management systems are severely inadequate in their ability to inter-operate amongst different functional entities. Albeit individually they may have been fine-tuned for optimal performance, these information systems are incapable of harmoniously interacting with each other. There are islands of information-blocks with minimal communication among each other. Thus for instance, integrating the Patient Records database with the hospital's Financial department is a tedious exercise, needing several manual steps to retrieve/process the electronically stored records. Often the same data gets stored in different systems. This leads to the problem of data getting updated in one system, but not in the other, causing data inconsistency. For example, if the Human Resources Employee system is not adequately integrated with the Health-care Information System, the staff data concerning access privileges may be stored separately in the two systems. As a security leak, even former employees could log-in and retrieve confidential patient data, if the user accounts were de-activated in one system but not in the other . . . . The main rationale for this drawback is that currently there is no extensible and customizable information system that fosters development of health care information systems which support inter-operability among diverse standards-compliant modules.

Legacy health care information management systems have limited incorporation of security in terms of data integrity and long-term data retention. Re-engineering of medical information systems is quite a challenging notion for organizations in the health care industry, due to technical complexities as well as the general reluctance to change. Other observed deficiencies include challenges of scalability and redundancy, with the growth in the sheer volume of data of the order of millions of records handled by larger health care organizations.

Problem of Building Extensible Health Care Applications

There have been many approaches to develop standards pertaining to various domains of health care arena like DICOM in image communication and HL7 in health care data communication. Both of them define standards for communication between heterogeneous health care applications. But their efforts for the definition and development of a middleware operating system that could serve as a platform to meet the relevant industry standards and ease the building of an enterprise-class health care information systems have been inadequate.

On a different note, CORBA Med from Healthcare Domain Task Force (HDTF) of the Object Management Group (OMG) defines a set of object-level standards (by defining standard interfaces). While distributed objects form an effective means to achieve interoperability, this does not fully address the problem of developing an enterprise level health care application conforming to the global standards. CORBA Med defines a standard for component-based architecture but fails to provide a ready-to-use platform and also makes the task of writing CORBA Med compliant components, quite tedious. Another neutral platform framework for building health care information systems is the Riche frame work from Group Riche overlaid on top by the DHE (Distributed Healthcare Environment). The Riche framework and DHE are too general and provide set of tightly coupled components, rendering the framework highly domain-centric.

A unique observation of the health care information systems across the globe is the diversity found in the workflow of health care institutions compared to other domains like BFSI (Banking, Finance, Security and Insurance). Existing applications need approximately ten times more work than the original efforts expended for tailoring it to meet the needs of global clients. A simple example depicting this scenario is the introduction of a mandatory Financial Clearance before admitting a patient or ordering of patient-services. Only a workflow oriented, rule-based middleware that is configurable at the higher level [i.e. Application layer] can address these issues.

Compared to the pace with which new technologies are being introduced minimal efforts are being devoted to link and use these technologies in the health care arena. This phenomena can be illustrated by use of the wireless technology in hospital information systems. Although the innovative wireless industry is booming with newer applications for the health care industry, very little standards are defined. The options available are often not viable in terms of their cost effectiveness and incompatibility to interface with existing frameworks. Similar is the case with Telemedicine that has immense potential but seen minimal field deployment due to lack of open standards and supporting frameworks. Vendors should be able to design applications for health care industry based on an open, extensible framework similar to the development of applications for the Windows or Linux. OS platforms.

A major drawback of the current HIS scenario is the use of individual ERP packages for many of the indispensable components of health care information systems like the inventory, payroll and human resources management. A tiered approach with a domain-neutral lower tier and domain-specific upper tier, together supporting applications at the highest tier can be a solution to the problem. For example, all the modules of the higher tier can use the services of a rule based flow control system defined in the lower tier.

What is clearly needed is a methodology/framework to build healthcare software applications that are well-integrated with each other, that provides accurate and dependable updated health care information in real-time, while being resilient to changes in business and legal requirements, adaptable and extensible with organizational needs, and provides disaster recovery. Also needed, is a system to make this possible with relative ease.

SUMMARY OF THE INVENTION

In a preferred embodiment a system and method for development of health care information systems is provided. A system for development of healthcare information systems comprising of a server with a middleware operating system stratified into multiple tiers composed of software components. Software components in one tier interact only with those in the adjacent tier. The higher tiers provide Application Programming Interfaces (API) for development of software specific to healthcare information applications, while the lower tiers provide functions of storage, monitoring, communication, security, management, data back-up, and recovery of health care information.

In this health care middleware operating system (HMOS), the first or the lowest tier, namely the Foundations tier, interfaces with standard platforms such as J2EE and .NET and provides core operating system functions of resource allocation, process scheduling, memory management including caching, data storage, back-up and recovery, and communication services. It also includes Workflow Engine and Rules Engine. The second tier is the Domain Services tier, which interfaces with the Foundations tier, which are populated with co-operative software components to guarantee Quality of Service (QoS) requirements of security, privacy, latency and reliability utilizing the Foundations tier and provides services including Clinical Data Retrieval, Clinical Data Acquisition, further providing API and domain-specific customizable rules-engines for development of application software for health care information systems.

The Foundations Tier [FT] of HMOS comprises of
Authentication and Authorization
Monitoring
Messaging
Auditing
Scheduling
Resource allocation
Knowledge Integration
Image Sound & Video Management
Back-up and Disaster Recovery Services The Domain Services Tier [DST] of HMOS provides APIs that are customizable and compliant with standards. The APIs provide for development of health care applications comprising of:
Drug Interaction Information store with APIs to access and operate on the stored information
Terminology services for interpretation of health care related terminology
Workflow Services
Rules engine for specifying portions of behaviors of health care applications
Natural Language Processing module for natural language understanding and translation between multiple natural languages
Notification module for communication between modules in the DST tier
Compliance software module for Digital Imaging and Communications (DICOM) standard,
Compliance software module for Health Insurance Portability and Accountability Act (HIPAA) standard,
Compliance software module for International Statistical Classification of Diseases and Related Health Problems (ICD),
Compliance software module for Health Level Seven (HL7) ANSI standard,
Compliance module for SNOMED multi-disciplinary standard vocabulary designed by clinicians,
Report management service using CPT codes
Module for Clinical Data Documentation System (CDS) for capturing and retrieving medical diagnosis details of a patient
Patient Care Management
Patient Identity Management (PIM)
Imaging Modality Management and Picture Archiving and Communication system
Security management
Inventory and order management service In the preferred configuration of HMOS, the method of developing health care applications to guarantee Quality of Service (QoS) requirements of security, privacy, reliability comprises of the following steps:
using a library of object-oriented programming classes to create new data objects
using a library of object-oriented methods to create an application to operate on the data objects created
automatically verify that the application created is compliant with standards and that it satisfies QoS requirements.

In the preferred embodiment, a method for communication among various software components comprises of steps based on publish-subscribe model as follows:
Every software component publishes its availability of data and services. A subscription manager keeps a record of which software components would like to subscribe to sets of data and services at any time at any time, if a software component requires or publishes data or services events are triggered for the data and service exchange to be executed. A permanent destination is set up for all outgoing messages, the response destination could be associated with an automatic persistent store, and therefore all outgoing messages could be sent persistently with guaranteed message delivery.

In the preferred embodiment, a method of scheduling tasks committed to by various modules ensures that every temporal and resource constraints is satisfied thus providing QoS guarantees.

In the preferred embodiment, a system for providing security for health care information called Globally Controlled Locally Managed system as part of the domain services tier comprises of the logical division of the security control called Security Domain and the Security Domain Administrator (SDA) wherein the application will be globally controlled by one administrator and he/she will be creating and assigning privileges to SDA and the SDA locally manages the users under their Security Domain.

The API at higher tiers is designed to make sure that any health care application developed using the API is compliant with health care protocols namely HL7, DICOM, HIPAA, ICD, CPT for seamless integration of multiple disparate health care information systems developed using the HMOS. A system part of the domain tier for capturing the entire medical diagnosis details of a patient and the system includes the different steps for capturing the clinical as well as the diagnostic, research information on a patient.

In the preferred embodiment, in the higher application tier, using the API provided by domain services tier are a set of software application modules that provide
- automated mechanisms for admission, discharge, and transfer of patients.
- purchase order creation and communication for both materials and drugs.
- Electronic Medical Records Management Module (EMR).
- Patient Care Management Module (PCMS).
- authentication and authorization using smartcards and biometric devices.
- side effects of drugs, interactions among drugs, and interactions among drugs and food interfaces with the database in Foundations tier through the domain services tier
- telemedicine for remote medical diagnosis and treatment with integrated video conferencing.

BRIEF DESCRIPTION OF THE DRAWING FIGURES

Figure 2:
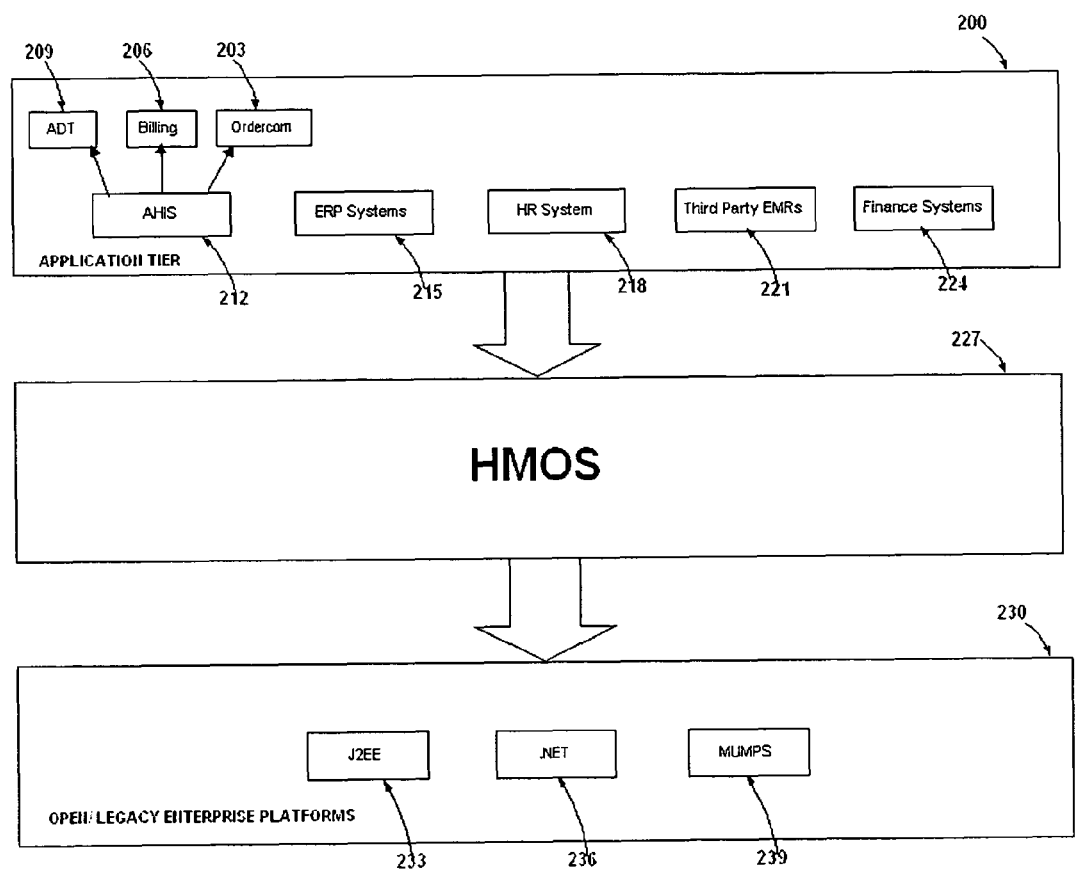
Figure 3:
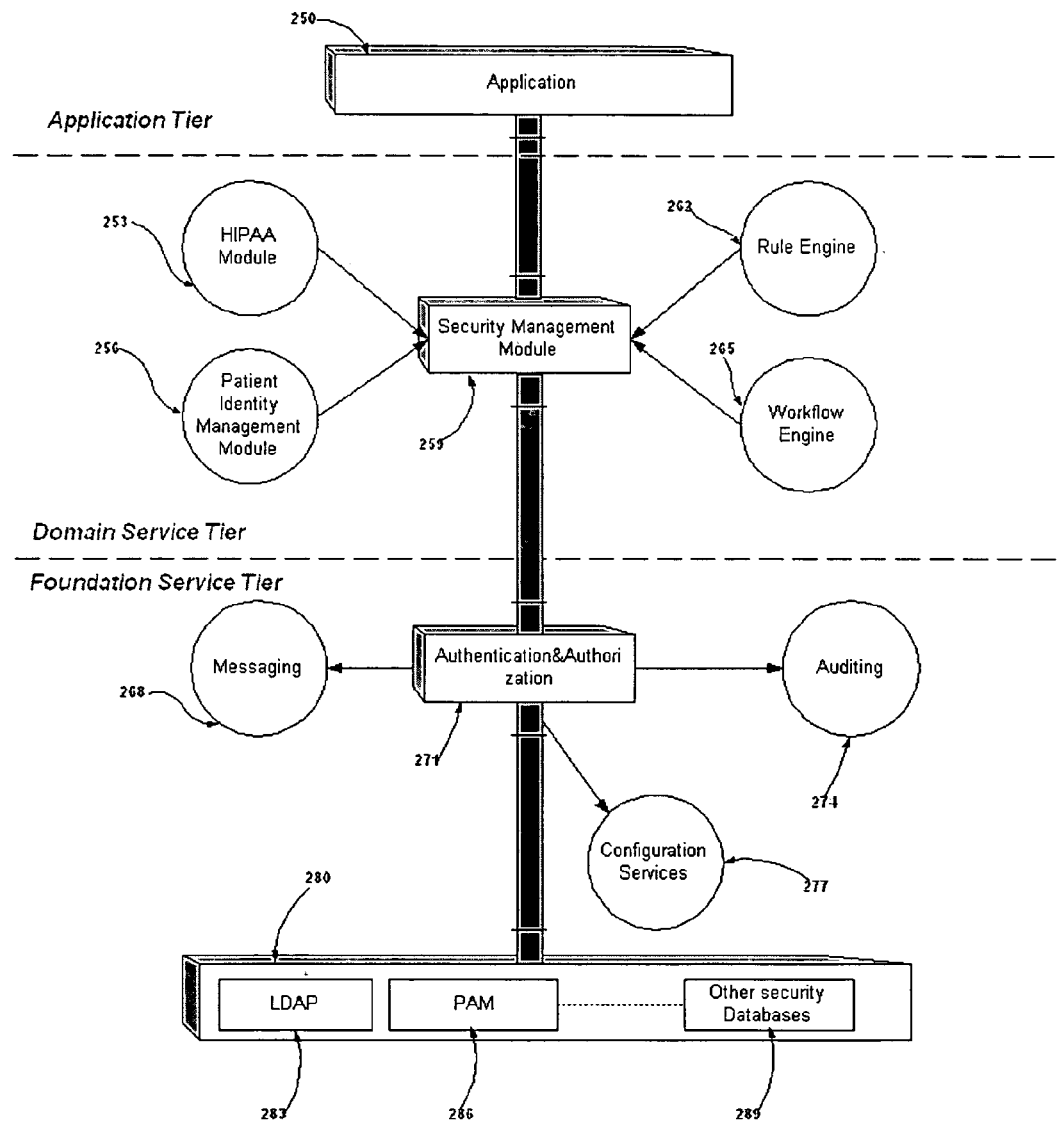
Figure 7:
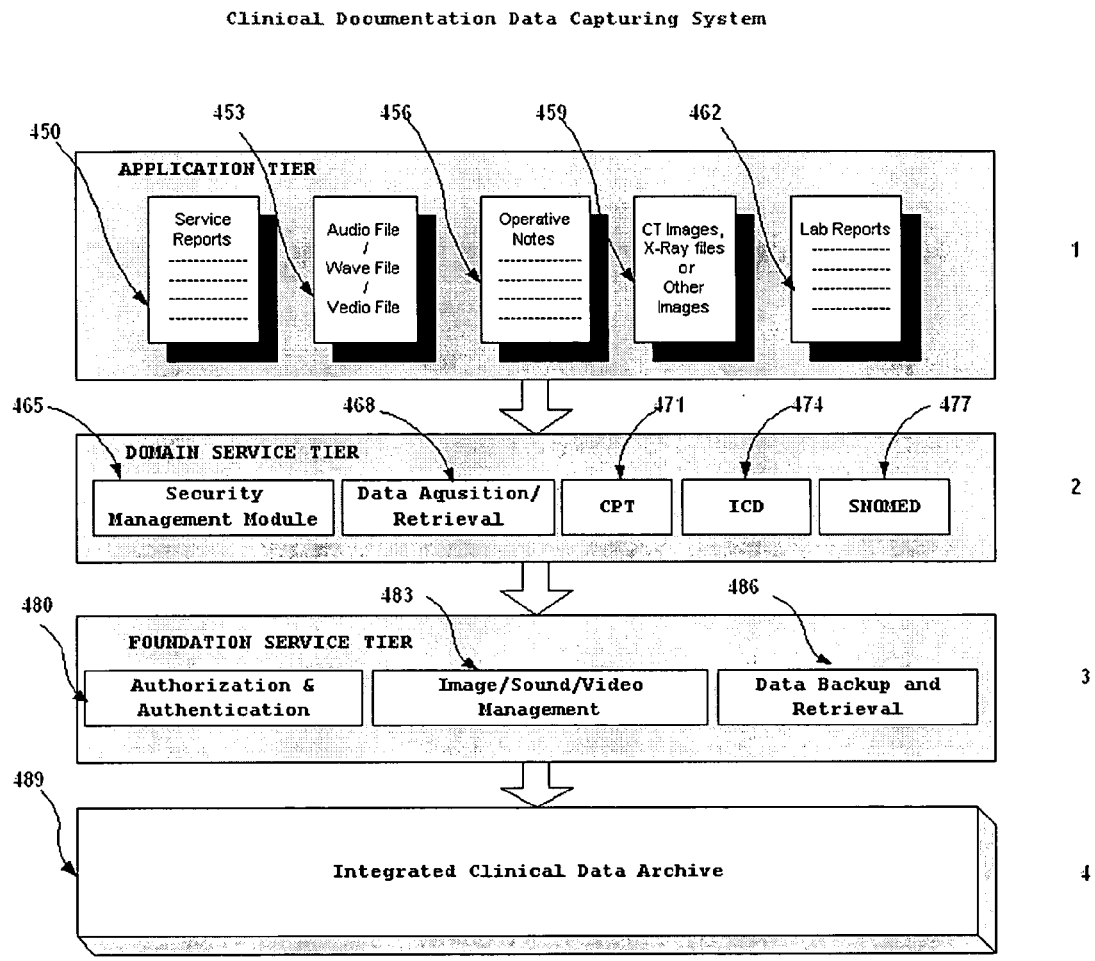
Figure 8:
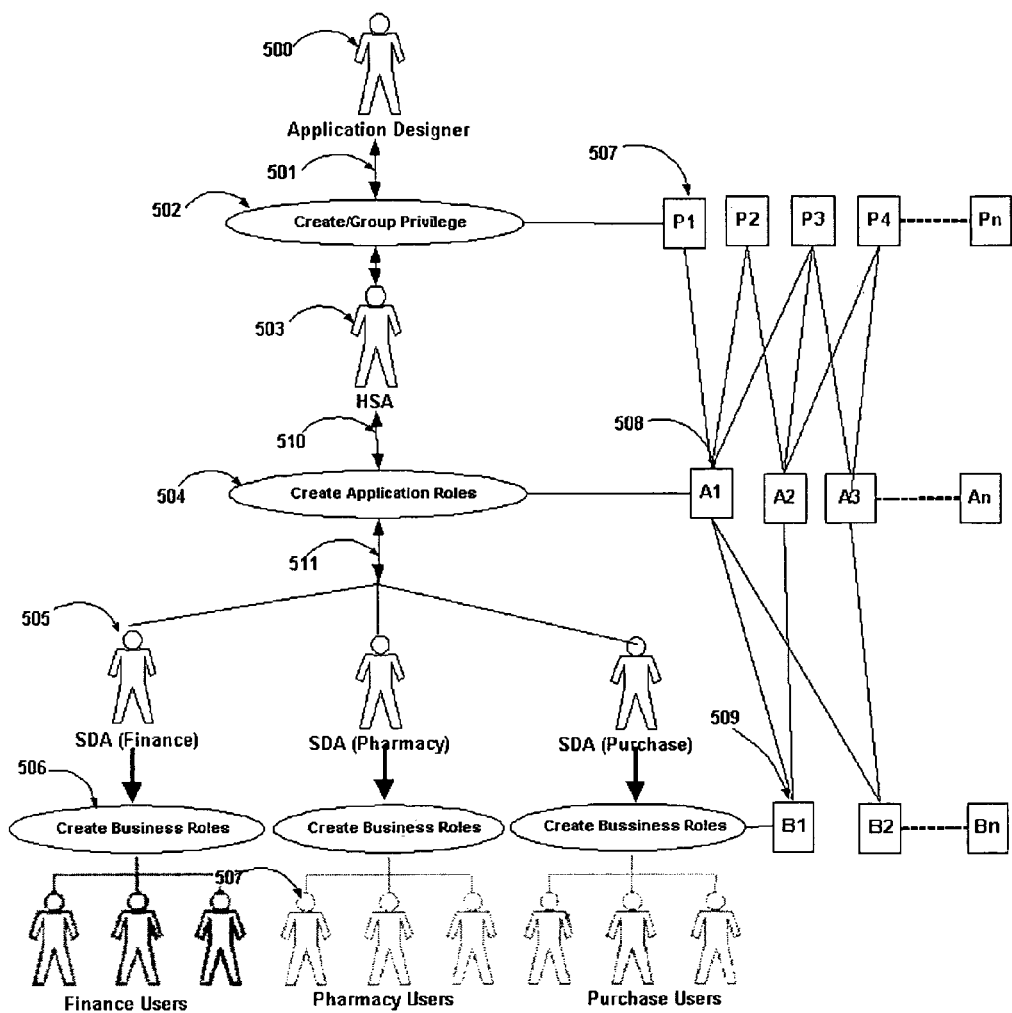
Figure 9:
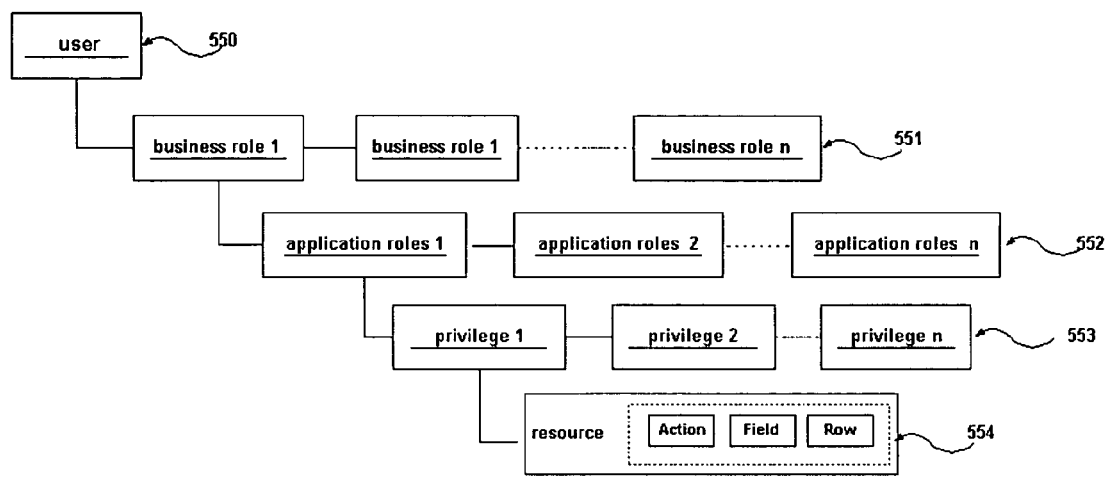
Figure 10:
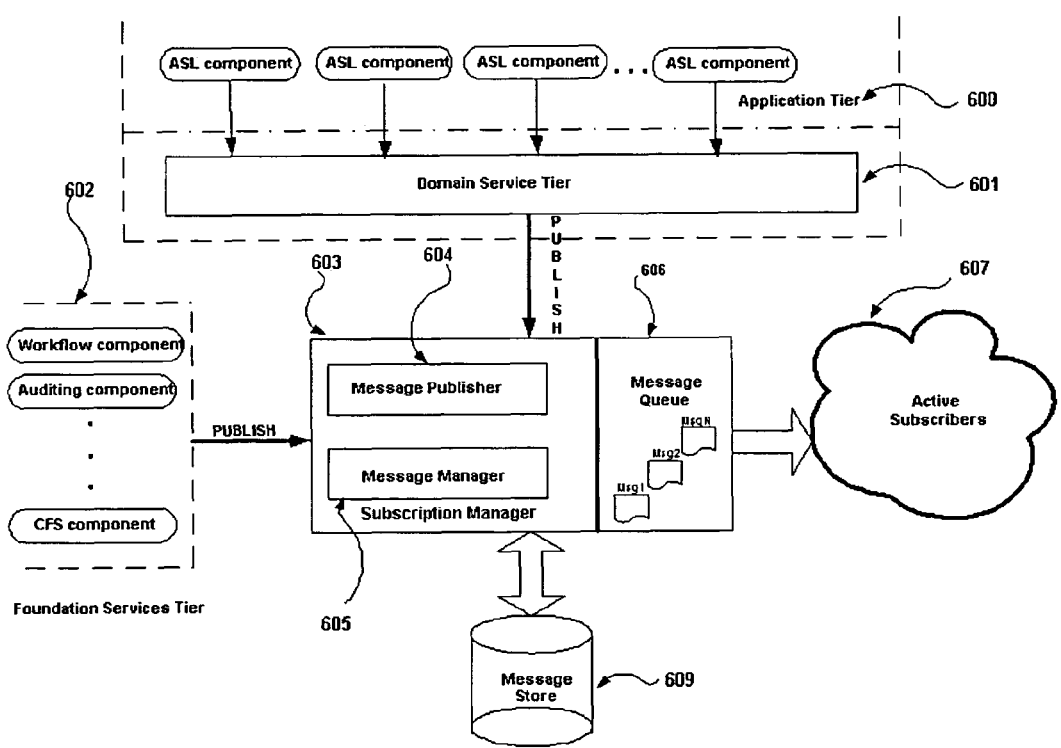
Figure 11:
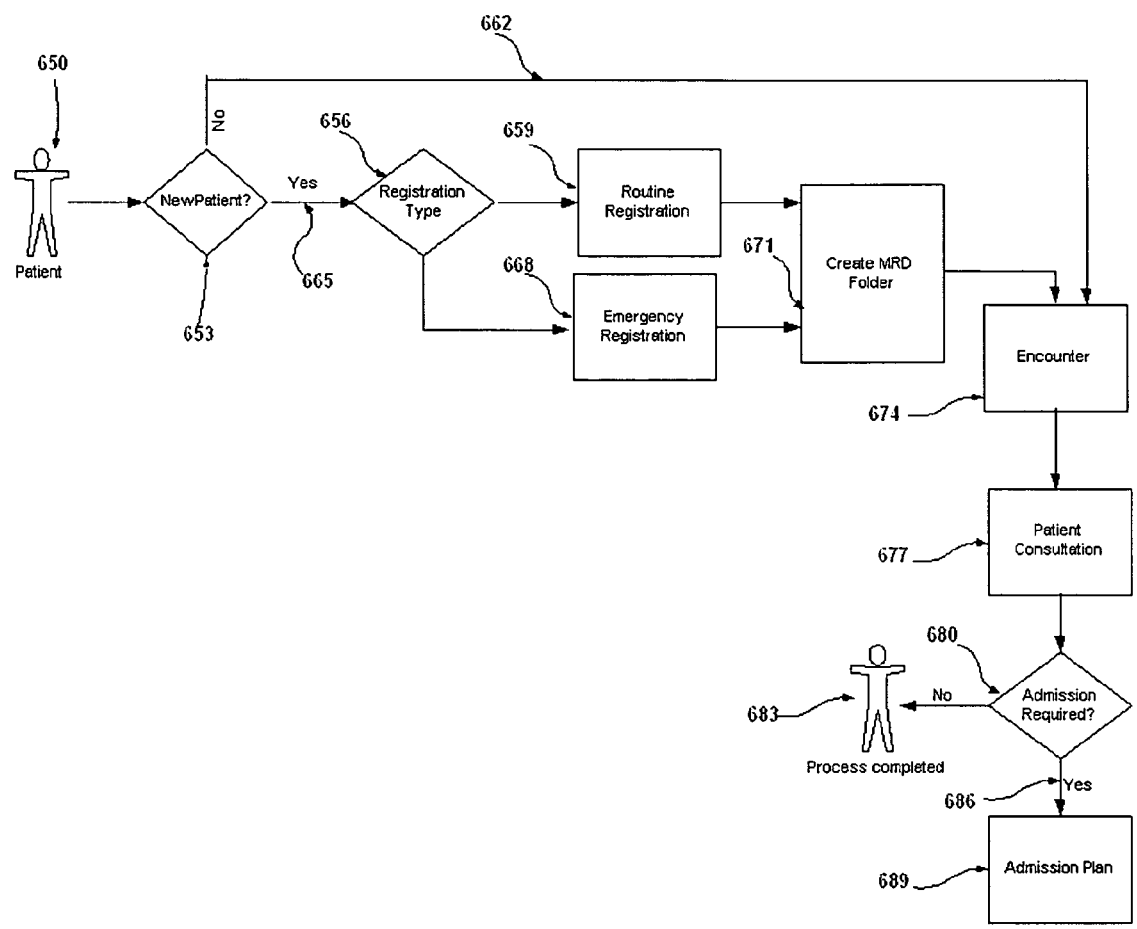
Figure 12:
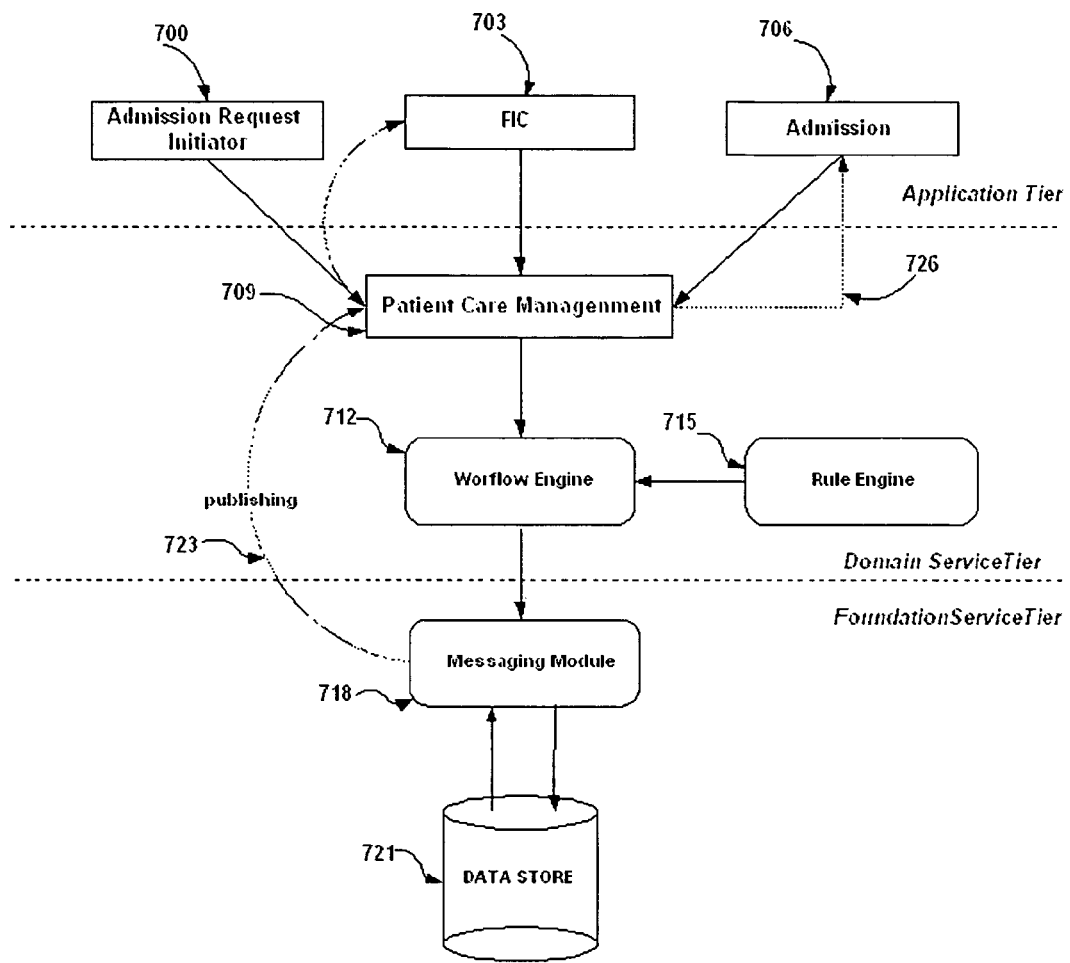
Figure 13:
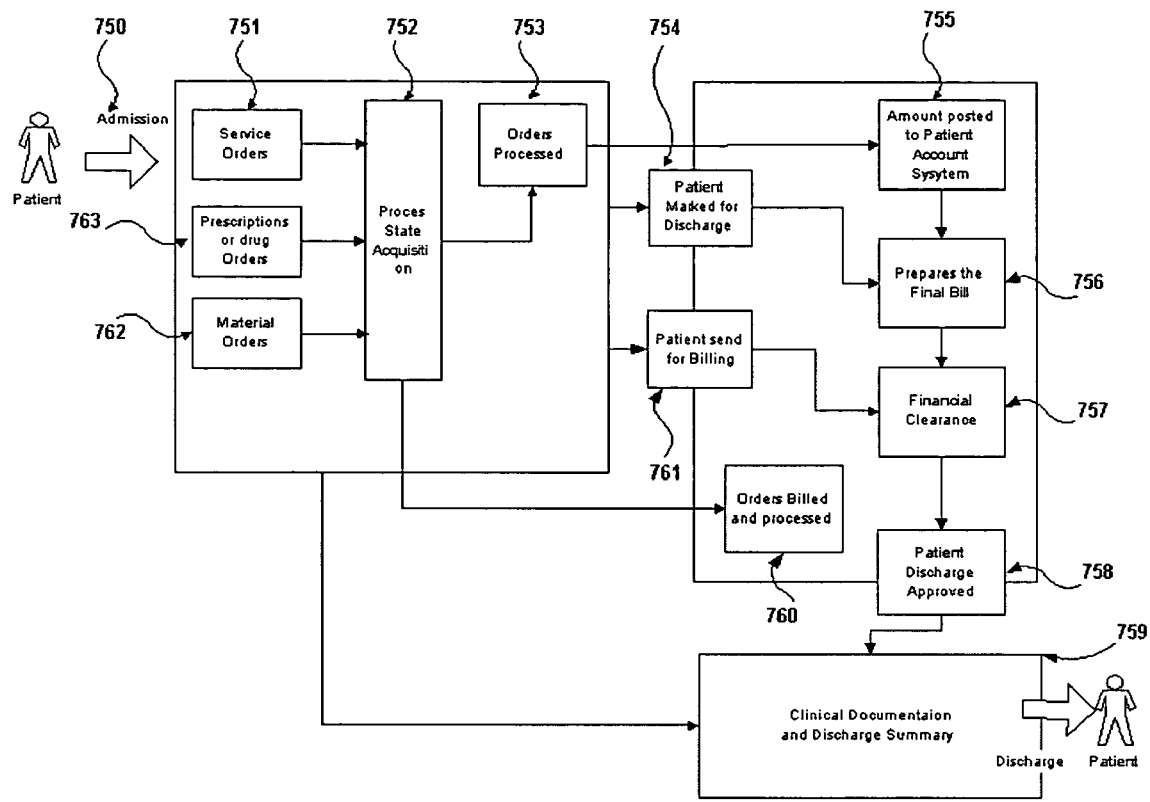
Figure 14:
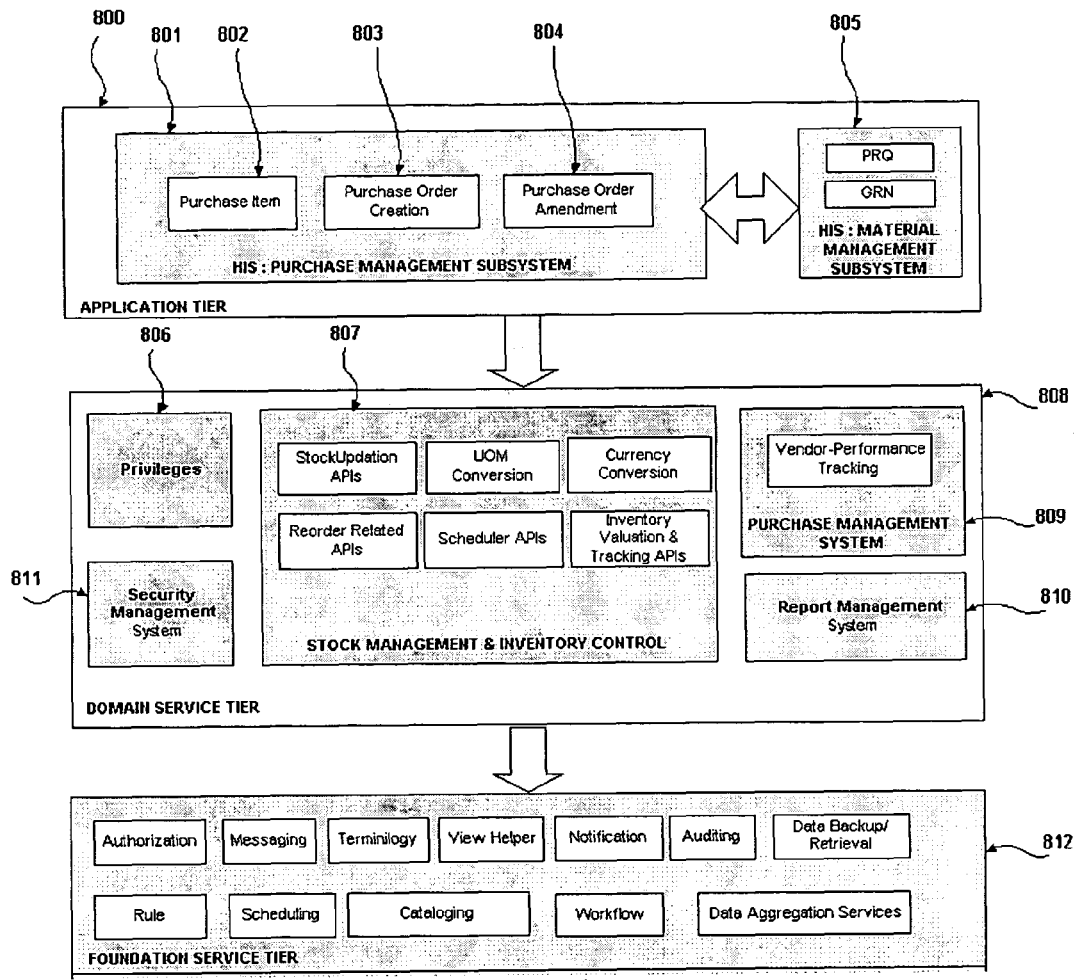
Figure 15:
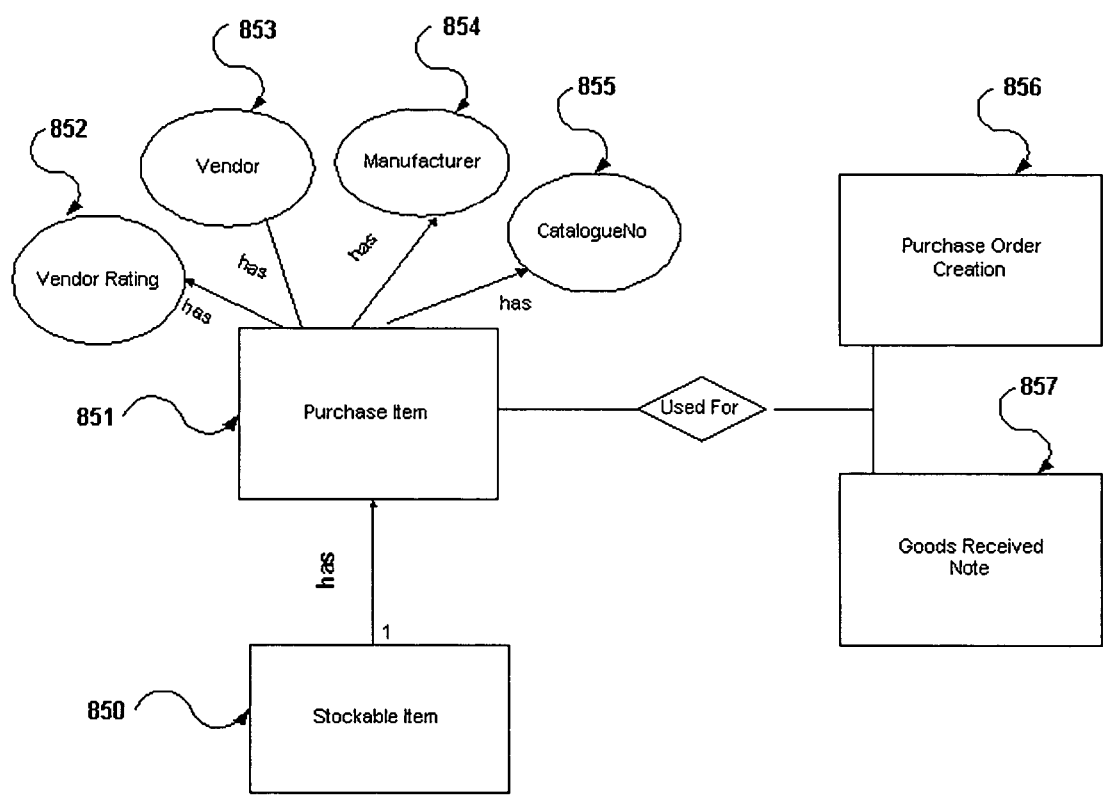
Figure 16:
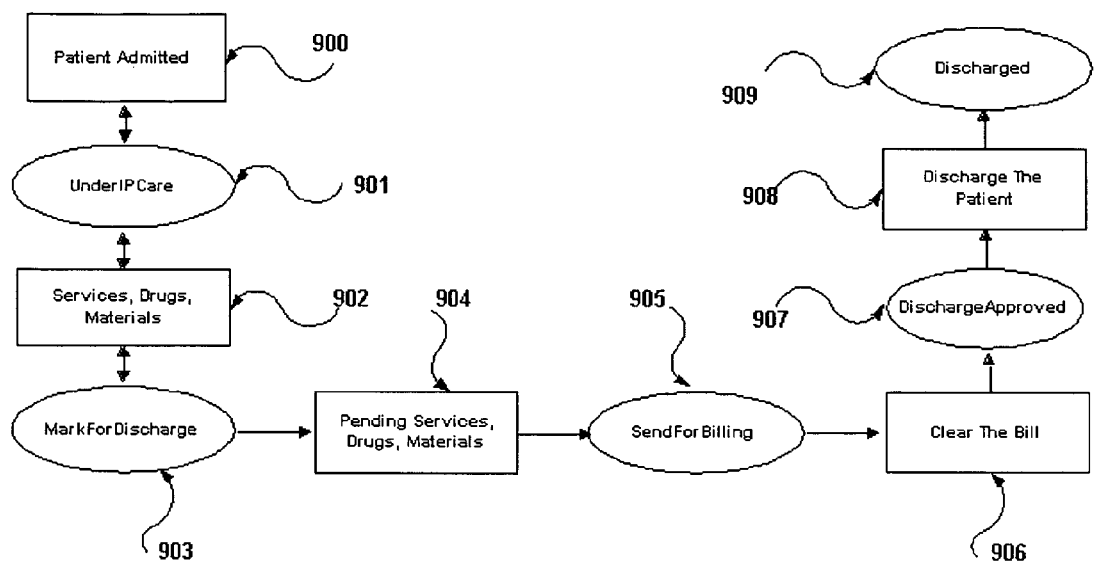

FIG. 1 is the high-level architecture of the Health-care Middleware Operating System (HMOS) that describes the various tiers.
FIG. 2: depicts how HMOS supports applications and platforms.
FIG. 3 Security Architecture of HMOS
FIG. 4: Scheduling Diagram of HMOS
FIG. 5: Terminology Services
FIG. 6: Clinical Documentation Frameworks
FIG. 7: Clinical Data Acquisition.
FIG. 8: shows an outline of the Globally Controlled Locally Managed (GCLM) Security System
FIG. 9 depicts the Elements and Composition of GCLM module.
FIG. 10: Publish/Subscribe Model
FIG. 11: Patient Admission Flow Chart
FIG. 12: Workflow based Patient Admission Process in HMOS
FIG. 13: IP Billing Workflow
FIG. 14: HMOS Purchase Management System Architecture
FIG. 15: Concept of Purchase Item.
FIG. 16: Patient Care Management

DESCRIPTION OF THE PREFERRED EMBODIMENTS

Introduction

An operating system is a system that manages resources within a computing machine. Executions of applications on a computing machine are coordinated and managed by the operating system. Operating systems functions include process scheduling and resource allocation. Middleware is a system that provides a uniform interface for applications to be developed for execution on multiple and disparate computer-programming platforms. Quality of Service (QoS) is often used to define a level of performance of a computing and communication system. Typical performance parameters are latency and throughput.

The present invention called Health care Middleware Operating System (HMOS) is a middleware with operating system functionalities designed to provide a substratum to develop health care information systems applications, which are customizable and reconfigurable. In the present invention we extend the typical notion of QoS to include security, privacy, latency, satisfaction of real-time constraints, and high-availability and provide guaranties to satisfy QoS requirements imposed by healthcare applications developed using HMOS. A preferred embodiment is shown in FIG. 1.

Health-care Middleware Operating System (HMOS)

Health care Middleware Operating System (HMOS) (FIG. 2.227) is a middleware operating system designed to provide a substratum to develop health care information systems applications, which are customizable and reconfigurable.

HMOS is comprised of 3 tiers:

Foundation Services Tier (FST) (FIG. 1.157) comprises of modules with operating system functionalities such as resource allocation and scheduling, and module with middleware functionalities such as messaging and knowledge integration. FST interacts directly with an underlying programming platform including generic enterprise-class frameworks including J2EE, .Net, and healthcare specific frameworks such as Mumps.

Domain Services Tier (DST) (FIG. 1.100) comprises of modules with middleware functionalities such as patient care and identity management, compliance with healthcare standards, and security management. DST provides Application Programming Interfaces (API) for developing healthcare applications.

Application Services Tier (AST) (FIG. 2.200) comprises of applications developed using APIs provided by DST will be known.

DST provides Application Programming Interfaces (API) for development of application software for healthcare information systems while the CST provides functions of storing, monitoring, communication, securing, management, backup, and recovery of healthcare information that guarantees Quality of Service (QoS) requirements of security, privacy, latency, satisfaction of real-time constraints, and high-availability.

An execution of a healthcare application at AST involves invocation of one or more modules in DST using the APIs provided by DST. The invocation of the DST modules may result in the invocation of one or modules in FST. Modules in FST may execute using functions and methods provided by the underlying programming platform. The resulting data from the execution of the respective modules in FST will be transmitted to the respective modules in DST, which in turn are transmitted to the corresponding healthcare application.

Foundation Service Tier (FST)

Major Operating System (OS) functionalities like memory management, scheduling, resource allocation and middleware functionalities such as object caching, messaging and object relational mapping belongs to Foundation Service Tier. The entire data store of all applications is associated with this Tier.

FST tier is comprised of the following functional modules.
Authentication and Authorization
Monitoring
Messaging
Auditing
Scheduling
Resource allocation
Knowledge Integration
Image Sound & Video Management
Back-up and Disaster Recovery Services Authentication and Authorization The Authentication sub-system has been developed to comply with all levels in the security hierarchy and features of typical state-of-the-art health care information systems. Authentication through smart card and biometric devices is also supported in the HMOS design.

The Foundation Services tier of the HMOS system provides a set of loosely coupled, API's that can be used independent of the underlying development platform. This inter-face tier enables domain services to authenticate and enforce access privileges upon HMOS-users. It has been implemented on a standard Pluggable Authentication Module framework (PAM). Public or Private-key based security mechanisms can be deployed within the Authentication sub-system. Pervasive HMOS system additionally supports Authentication through wireless and mobile computing devices.

Authentication and Authorization API's facilitate HMOS' Domain Service Tier to provide role-based, identity-based or privilege-based, highly customizable and configurable user-interfaces conforming to standard Security protocols.

Messaging

Messaging is used in HMOS for communication between health care applications or modules. Subscription manager controls the Messaging Domain of HMOS. This architecture proposes that a permanent destination is to be set up for all out going messages, the response destination could be associated with an automatic persistent store. So all outgoing messages could be sent persistently with guaranteed message delivery.

The activities performed in the application tier are published and managed by an entity called Subscription Manager where all the active users can subscribe the published messages. For example, as soon as a patient completes the registration, the ADT sub system of the Application Tier can publish that information so that the relevant Specialty/Doctor can prepare for the patient's arrival. Another example will be that of publishing the event of drug prescription so that the pharmacy people can keep the drugs ready before the patient's arrival.

Monitoring

FST tier's Monitoring Interface provides a re-definable scheme to effectively monitor resources of an HMOS system with a sophisticated notification rule set. The Monitoring module is user-configurable to schedule and set priorities for monitoring activities. Working in conjunction with Messaging interface, the Monitoring interface supports a real-time monitoring and messaging framework to detect and report alarms in the event of system failures. The events monitored are also user-configurable, so that HMOS also has the capability to deliver an effective and intelligent alarm management scheme. The domains monitored by the HMOS alarm management sub-system include user-access, performance, data & network availability.

Monitoring module using algorithms from the AI discipline is capable of learning from an event's experience and sends advance messages, in anticipation of the event's outcome. This facilitates a highly scalable and extensible design, supporting a wide range of open software and hardware platforms. In a plug-and-play fashion plug-in of any new software or hardware, can be automatically detected by the Monitoring interface.

Auditing

The Auditing Interface sub-system empowers HMOS to monitor and log any/all changes in data and service settings in an untarnished manner. The interface contains a set of configurable APIs that can define the level of auditing needed for different areas of the HMOS system. The Auditing interface is tightly coupled with the Security features of HMOS. Administration, monitoring, maintenance and storage of the logging activity are carried out in a restricted and secure environment. The Auditing module is endowed with built-in intelligence to determine the severity of all changes and raise appropriate alarms by collaborating and communicating with the HMOS Messaging service.

An important and distinctive feature of HMOS is that for all transactions processed by the Auditing module, snap-shots of pre-change data and post-change data, along with the delta of change is saved. Furthermore, information elements pertinent to the data-changes, i.e. who (user name)—when (time)—where (IP Address—Station Name) information are also saved for data archives.

Knowledge Integration

Knowledge Integration is a unique feature of HMOS concerned with the processing and management of information from diverse multiple sources in an open, yet secure environment. Knowledge Integration specializes in the provision of multiple-source information delivery solutions, and the individual components that make a diverse range of information sources visible in an open, yet secure, environment. This environment is set up using HMOS Connector Architecture (HCA). Here data and functional knowledge are extended through this knowledge based connector architecture that provides a means to represent as XML entities and functional knowledge as set of APIs. These entities get triggered, based on rule-based trigger points. All the external resources are pluggable to the HMOS only through this architecture. This leads to an easier and faster cycle for the development of scalable, secure, and transactional enterprise applications that require connectivity with multiple Information Systems. HCA has a structured connection pool such that it creates connections in an efficient manner and does not cause resource starvation. XML binding provides simple and platform independent means for the polydentate feature of HMOS.

Image, Sound and Video Management

HMOS provides standard interfaces for management of image, sound and video information. Along with clinical data these are managed just as text data, to provide an Integrated Clinical Data (ICD). HMOS furnishes a set of APIs associated with Visual and Sound functionality. The resultant adaptability enables HMOS application to manage the clinical document along with related information from image and sound domains. HMOS incorporates all standard archiving solutions for medical, scientific, and microscopy applications. This provides for HMOS-users to systematically develop database—a warehouse of intelligent clinical data that can be useful for any research or review/analytical studies. The strategic importance of this system should be clear—it enables creation of a true, paperless patient record.

APIs encapsulate all the functionalities for saving, querying and retrieving data from the image, sound and video resources. The recorded sound can be converted into corresponding text using a built-in voice recognition tool . . . . The APIs, furnish an added advantage to HMOS-users, to transform captured video images into frames, for archival. This can be extremely useful for Medical Transcription services. Image archival into a PACS system can be accomplished in various formats such as DICOM, JPEG, GIF, and TIFF. The APIs, for converting captured video images into frames and archiving it in any format, are an added advantage provided by HMOS in medical arena.

Data Back-up and Recovery Services (DBRS)

The DBRS ensures safety of data associated with HMOS. This system coming as an integral part of HMOS FST tier and it makes HMOS to face any type of disastrous situations related to data loss. Centralized control and administration is its main feature. It aims mainly on restoring the system in a bare minimum time even in the case of complete data loss, and to retain the system in its pure original transactional state with little user level interaction. For restoring procedure to work smoothly it uses a two stage backup procedure, one recurring in a daily basis and the other happens incrementally, according to the wish of database administrator. The backup taken incrementally even ensures the life of latest transactional data just before crash. As it implements a log based back up and recovery procedure we can relay it for even table level data loss. Thus the hierarchy of recovery ranges from the entire database to a single table. The daily back up procedure also provides provision for integration with OLAP and other Knowledge Integration Systems, which makes them synchronized with latest data. It also provides option for routine database checking for improved data integrity and security.

Another important feature of DBRS is that it can be accessed through web-based interface, which allows DBA to monitor and control (only necessary and limited control) the various status of backup procedure even from a remote. This is implemented under tight security realm so that no leak outs will happen any way under any circumstances. It also provides the facility to take back-up on portable devices like tape drives to ensure the security of data even due to natural calamities. This also provides reports to DBA in daily basis and even sends necessary acknowledgments through E Mail. Its also provides statistical data regarding the database such as size and various other information regarding results of the routine checking and updating.

The entire disaster recovery procedures are automated so that the latency time of recovery is reduced to the most possible extent. The backups are moved to remote locations and various copies are maintained at various geographical locations for further safety. The entire distributed storage of the backups and its fast retrieval during a recovery process is the main feature of DBRS. It automatically checks for the most recent versions of backups and recent transactional data to get a smarter snap shot. The various information about checkpoints at various time stamp levels is maintained to get the most recent updates in the database.

Scheduler

The HMOS scheduler (FIG. 4:326) is an integral part of the FST. Scheduling is concerned with the allocation of limited resources to tasks so as to optimize certain functions. It schedules all the tasks in the HMOS based on the various scheduling algorithms. These scheduling algorithms works on the basis of attributes specified in the configuration files of the Domain Service Tier. This feature enables the top-level services to schedule clinical tasks according to the local situation. The scheduler itself schedules all the core services and these tasks are not visible to the outer tiers. Other tasks that can be scheduled according to the entry in the configuration files in the DST and these entries can be modified on the basis of requirements. Also new tasks can be entered in the same file. The attributes in the file are name of the service, date, time and status. Applications can dynamically change the date time parameters specified there. This feature facilitates the applications to schedule and configure their jobs as they wish.

Apart from core service scheduling in a clinical environment scheduling of services and procedures in a proper way is essential for better patient care. So HMOS provides a fruitful and effective algorithm for each schedulable task.

In the area where scheduling tasks get much complex, like OT scheduling, HMOS uses algorithms that are evolved as a result of detailed research and in the mean time these algorithms strictly follows all medical standards.

Operation theatre activities such as pre-anesthetic check-ups, pre-anesthetic notes generation, recording anesthesia details, maintaining the list of procedures for various operations, recording operation details, and maintaining operation theatre availability, are important while scheduling the Operation Theatre. Basically some of the parameters for the above activities are depend on place and situation. So essentially for the smooth going of the work the system must have a facility to adapt with change. HMOS provides these features. I.e. as said earlier the scheduler of FST works according to the parameters specified in the Domain service Tier.

Scheduler Maintaining Quality Of Service

The scheduler also guarantees that every resource constraints are satisfied. Thus providing Quality Of Service for all the tasks that are to be scheduled. Each task is associated with a number of constraints and the scheduler notifies the task initiator in such a way that if the constraints cannot be satisfied within the current context, it will generate a precise indication of the reasons thereof, providing QoS guarantees. This can also be explained in terms of security measures taken by each individual module in the HMOS. Since quality of service is a set of methods and processes a service-based organization implements to maintain a specific level of quality. Also the notification of the scheduler to the task initiator is a classic example of maintaining QoS as key feature of the entire system.

Resource Allocator

The resource allocation is one of the most important features of an operating system. HMOS provides a uniform flexible interface that helps to allocate various resources required by DST services. Examples of resources are service processing time, queue buffer sizes, and high-level object resources. The HMOS utilizes resource allocation to satisfy QoS requirements. In HMOS, the resource allocator supports the allocation of multiple heterogeneous resources like beds, materials, drugs, operation theaters, doctors, and nurses. When the resources are no longer required, the allocated resources are released and will be available for reuse.

Domain Service Tier (DST)

The Domain Service Tier (DST) (FIG. 1.100) hides the lower level complexities of the Foundation Service Tier from the Applications Services Tier(s) (AST) (FIG. 2.200). The DST provides APIs to develop health care information systems applications.

The DST comprises of the following software modules:
Drug Interaction Information store with APIs to access and operate on the stored information
Terminology services for interpretation of health care related terminology
Workflow Services
Rules engine for specifying portions of behaviors of health care applications
Natural Language Processing module for natural language understanding and translation between multiple natural languages Notification module for communication between modules in the DST tier Compliance software module for Digital Imaging and Communications (DICOM) standard, Compliance software module for Health Insurance Portability and Accountability Act (HIPAA) standard, Compliance software module for International Statistical Classification of Diseases and Related Health Problems (ICD), Compliance software module for Health Level Seven (HL7) ANSI standard, Compliance module for SNOMED multi-disciplinary standard vocabulary designed by clinicians, Report management service using CPT codes Module for Clinical Data Documentation System (CDS) for capturing and retrieving medical diagnosis details of a patient Patient Care Management Patient Identity Management (PIM)

Imaging Modality Management and Picture Archiving and Communication system

Security management

Inventory and order management service

Drug Interaction Information Store

The Drug Interaction Information database will give instant access to information about the adverse reactions for most of the drugs. This also includes the information about drug-to-drug interaction. The classification also includes various categorizations based on patients' age such as geriatric, as well as the clinical areas under which the drug is widely accepted. It also provides information about preventable drug reactions and the available information about clinical trials for each drug. The clinical research data regarding the food-drug interaction is another indispensable part of this tier. This part provides research reports regarding the analysis of chemical structures of drugs and its metabolic pathways with the help of bioinformatics analysis. Thus this part provides various information regarding biochemical reactions and the inferences that can be used in further researches.

Terminology Services

Figure 5:
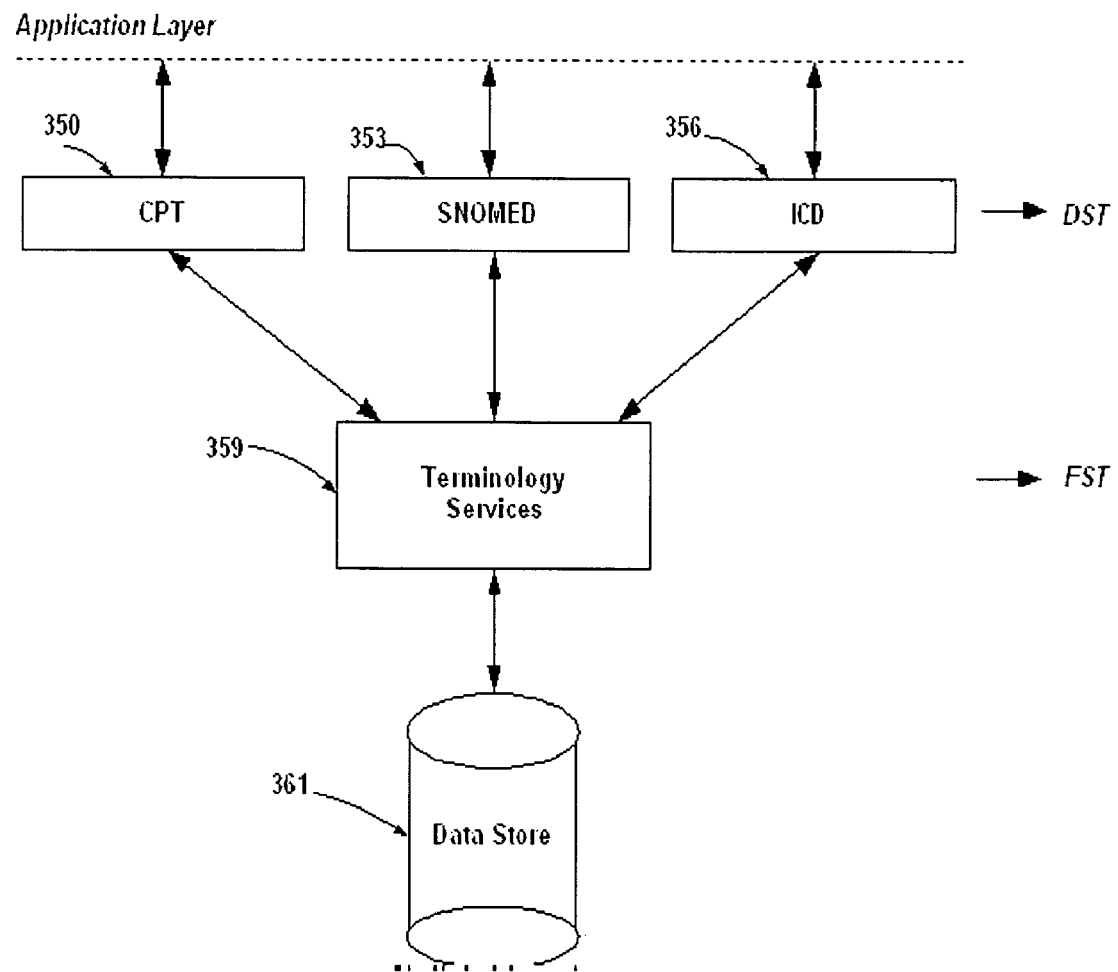

Instead of setting each repository for the CPT (FIG. 5.350, SNOMED (FIG. 5.353) and ICD (FIG. 5.356) the HMOS handles these DSL services using its Terminology services module. The Terminology service provides the repository for all the clinical standards. This includes a Mapping Service that helps to map the terminologies of different standards, so that any application built on top of HMOS can communicate to the inner services using any of these standards. Since the terminology services works as a base or all the clinical terminologies, the DSL is able to accommodate any newer standards without affecting the core structure. This type of architecture makes HMOS viable to integrate different systems using different standards.

Workflow Module

Business process in healthcare enterprises are modeled as state-machines undergoing various state changes within HMOS. HMOS provides a Workflow Engine in DST that allows to define new business processes and link them with existing business processes. Each business process is split into different steps, called process states. Triggers that alter the state of the process are called events. Events may arise from within HMOS, through user interaction or from an external system. Change of state from one state to another is referred to as state transitions. Workflow Engine in DST provides an XML-based configuration mechanism to define process states, events and state transitions.

Any business process within applications in AST of HMOS can be modeled using the services extended by the Workflow Engine. Example of a business process can be scheduling admission for a patient for a performing a surgery. Admission scheduling involves doctor's order for admission, getting available date of the surgeon, getting financial clearance from the insurance company, getting receipt of necessary tools and instruments for the surgery etc. Events can include doctor changing the date of his availability, a special consumable item needed for the surgery not being available in stock etc. These events can alter the outcome of the business process. These events and transitions can be coded in the HMOS workflow configuration files. With the changes in the configuration, admission scheduling application in AST gets dynamically configured to reflect the new configuration.

Rules Engine

Rules provide a method of dynamically changing the characteristics and behavior of applications developed using the APIs provided by DST. Thus rules can be modified, added, and deleted on the fly while the health care application is running. Rules are stored in a rule base, and the rules engine ensures that the set of rules are consistent with each other, that there is no contradiction between any two rules.

The syntax of the rules is as follows:

{Patterns to be matched} "->" <Actions to be taken>

The pattern to be matched on the left hand side may consist of regular expressions. The action to be taken contains software program data and method invocations. Thus when an application in AST or a module within DST requires to consult the rules engine, the module or applications send a pattern of data in question and the rules engine invokes the action to be taken in the form of software program method invocations if the pattern matches any of the rules in the rules base. Thus, applications can be customized or reconfigured while they are still executing to the extent that the rules engine allows based on the rule base.

Modules for Compliance with Health-Care Standards

Compliance with health care information standards is imperative for interoperability and acceptance by health care industry. The DST comprises of software modules that implement health care industry and federal standards such as HL7, DICOM, ASTM, ICD, SNOMED, CPT, and HIPAA. Each of these modules provides APIs for development of health care applications in AST. Therefore any application developed using the appropriate API is ensured to comply with that specific standard. SNOMED Clinical Terms is a multidisciplinary electronic vocabulary designed by clinicians for clinicians. In HMOS each medical term has a SNOMED basis. This feature is crosschecked in the Domain Service Tier so as to keep the Clinical integrity of the data.

The integrity, security and privacy of the clinical data are handled using a set of HIPAA compliant rules. The HIPAA based rules are designed to protect the privacy, authenticate, authorize, and maintain integrity. These are necessary to protect against the threats of eavesdropping, manipulation, impersonation and unauthorized access to health care information of individuals.

Imaging Modality Management

The Imaging Modality Management capability is achieved through a set of a DICOM APIs in the Domain Service Tier. An application at AST uses APIs provided by the Imaging Modality Management module to query and retrieve images from remote radiology imaging modalities using DIMSE (DICOM Message Exchange) protocol. Furthermore, it provides Picture Archiving and Communication System (PACS) facility for application at the AST.

Clinical Data Documentation

The Clinical Documentation System captures all the medical diagnosis details of a patient (like, Primary diagnosis reports, Service Order reports, Operation Notes from Operation Theatre, Other patient care reports, Discharge summaries etc.) in a structured and advanced way as the patient walks through the various nodes of the workflow of the hospital. The Clinical Documentation System is represented as in the FIG. 8.

Figure 6:
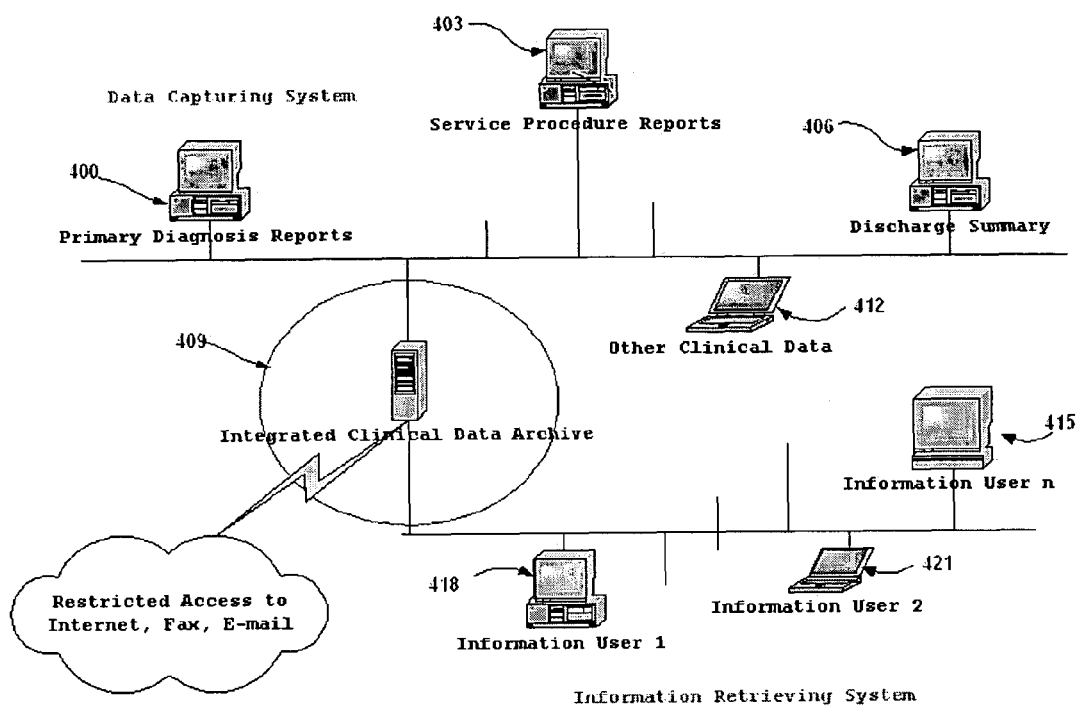

The Clinical Documentation system uses two separate workflows for Data capturing and Data retrieval. The Data capturing details includes various methodologies to acquire the widely spread patient's clinical data, either electronically or by manually. By manual ways the data can be input through clinical templates, and saved to the clinical data store. Also by electronically it can be gathered by setting the properties of the controls of clinical template such a way that it automatically pop-up clinical data previously entered. The Data Capturing System of the above is shown in FIG. 6.

The above said clinical data is captured in this Advanced Clinical Documentation System in many ways.

1. Through user defined clinical templates. By template we mean data entry forms. Each template has many numbers of data entry control boxes with properties like text justification, left and right indenting etc. There are many numbers of controls, which will accept specific type of the clinical data in different formats, like Combo boxes, Rich edit boxes, Text areas etc. The added advantage of such templates is that the users of the Clinical documentation system can freely design the varies clinical data that has to be collected though this templates. The user can add/modify/delete controls from a template arrange their position and change their properties, as he/she likes. The users also can edit the header and footer of the template and they can arrange the printable format of the saved documents.
2. The Image annotation control is an important tool available in this Advance Clinical Documentation System, which will allow the users to upload specific images of the patient like, X-ray images, CT images or Endoscopy images and annotate on those images with required clinical data. The added advantage of these image annotation controls is that the user can incorporate them in data a capturing template, which is discussed above.
3. The ICD (FIG. 7 471) (International Statistical Classification of Diseases and Related Health Problems, R10) and CPT (FIG. 7 474) (Clinical Terminology and Procedural coding system) coding systems are implemented as controls in the above said Clinical Documentation system. The advantage is that the user will get the ICD and the CPT coding conventions as single controls, which can be incorporate in the data capturing templates as per the requirements. Also they can retrieve the clinical data based on the ICD and CPT codes in later times.
4. Audio recording and replaying facility is another advantage of the said Advanced Clinical Documentation System. The doctors and/or in-charge medical personal can input the diagnosis and other reports through a microphone, which will save as an audio file in the Integrated Clinical Data Store, and that can be replayed for dictation and/or medical transcription in the later time. The audio replaying system is very advanced, which includes the facility to Pause, Replay etc.

Whenever a new template is created or a template is modified, it will ready for use in the system.

The Clinical Documentation System allows the user to capture clinical data from different direction of the workflow, such as, Primary diagnosis details of a patient can be collected from the doctor's room, and/or the operative notes can be collected directly from the operation theatre itself and so on. This means the system is flexible and scalable for any hospital's workflow. The collected clinical information of the patient is stored in the Clinical database in a normalized and structured format.

The security policy of the Clinical Documentation System restricts the insertion, modification and deletion of the clinical data from the Clinical Documentation System Archive. The authorized users (Security Domain Administrators) can define a security policy for the end user inserting and accessing the clinical data through the given interface of the Advanced Clinical Documentation System. The system supports: service center level, template level, and field level security policy to the end user those how are entering the clinical information. There is provision to define security policy for authorized access of Internet for sending the clinical information in the Clinical Documentation Archive as E-Mails and also for sending it as Fax. The integrity of the archived clinical data is kept to the higher priority through the basic security policies defined in this system.

Reports Management Module

From Clinical Documentation Archive, clinical information is retrieved and reports generated by the reports management module in different formats as follow:

1. As printable reports: The printable reports of the clinical data of a patient can be taken for any purpose like giving to the patient and/or sending it to other physicians. The printing of such reports can be restricted by define such a security policy.
2. Informative and research oriented reports: The cumulative reports and research oriented reports suffices to access a wide range of the clinical data saved in the data store. The accession of clinical data can be restricted using the security policy. The authorized user can have an advanced searching facility in the clinical database for specific type of reports they would like to have.

Graphical representation: The graphical reports can be viewed satisfying a condition of the user, is important for research purposes. The authorized users can take such reports of many kinds like Pie charts, Bar diagrams, Line diagrams etc. for representing the data.

Patient Identity Management

The Patient Identity Management System generates a unique identifier, which is used to identify a patient. An Identifier is a unique way of naming. A social security number, a patient number, and an email address can all be considered Identifiers because they uniquely identify a person. Similarly, a hospital's address, and registration number can be Identifiers for that institution because they can be traced back to that particular hospital. In middleware, Identifiers can be used to assign names in this manner, including abstract concepts such as software applications or entities like security levels. The entity named by an Identifier is known as its subject.

The HMOS patient identifier uniquely identifies the patient across any geographical barriers. The format is alphanumeric and the three major portions of the identifier are, 1. A unique geographical code
2. A unique Hospital Code
3. Local Patient Identification Number.

This feature becomes even more essential for telemedicine applications because it helps the system to distinguish the patients across the geographical barriers.

Security Management

Security subsystem of HMOS includes Authentication and Authorization module (FIG. 1 160) FST; Security Management module (FIG. 1.148) of the DST and security administration applications that are built in AST using the DST APIs. Authentication and Authorization module of the FST also works closely in conjunction with Configuration module, Auditing module and Messaging module of FST. Security Management module of DST uses the services of the above-mentioned FST modules and works closely with other modules of the DST, most important of them being Workflow Engine, Rule Engine, Patient Identity Management and HIPAA module. Authentication and Authorization module in FST can interact with lower-level platform provided authentication and authorization mechanisms such as Lighwight Directory Access Protocol (LDAP) and Pluggable Authentication Module (PAM) module, and custom-made security databases.

HMOS is designed with security management of large health-care enterprises with multiple sites in mind. For this, HMOS provides a security authorization assignment and management method called the GCLM (Globally Controlled Locally Managed) security management. Design goal of GCLM provides for the necessary scalability and management ease for large healthcare enterprises. Structure, functionality and effectiveness of GCLM security management method is explained below.

In GCLM, the lowest granular unit of security right is called a 'privilege'. Application designers, with the help of domain experts, define the 'privileges'. Privileges can be action-level, field-level or object-level. Permission to use a particular menu item, perform a particular action in the HMOS system, view a report or initiate a workflow process are examples of action-level privileges. Privilege to view or modify a field in a user interface, see a particular column in a report are called field-level privileges. Privilege to view a particular instance of a business object (for a example, a purchase order with a currency value exceeding 10,000, a bill of amount 200 etc.) is called object-level privilege.

Lowest granular person or business process to which security is assigned (security assignee) is called a 'user' in HMOS. For a particular installation of HMOS, one user can be specified a HMOS System Administrator (HSA). (FIG. 8:503) HSA divides the entire user base into one or more non-overlapping Security Domains and assigns users into these Security Domains. HSA can specify an administrative authority, Security Domain Administrator (SDA) (FIG. 8 505), for each Security Domain. SDA inherits his or her rights from the HAS through explicit assignment.

All the managed assignments within each security domain may further be audited, restricted or controlled by the HSA.

Each SDA in her own right can further subdivide the security domain into smaller domains. This provides for a hierarchical organization of security domains. SDA in turn will act as the global controller for the newly created some domains within his or her domain and gets the full controlling authority over the new sub-security domains.

A special characteristic to note is, that even though a SDA has total security management control over all the users under his or her security domain, he or she is not limited to granting such rights to a user belonging to a different domain. This provision provides the flexibility that is needed in large enterprises where functional privileges are not always hierarchically granted. A user may be serving cross-domain tasks for the organization. Each of such cross-domain security grants are treated as special audit points by the HMOS and are thus regularly audited by the HAS.

Privileges are named to reflect the application units that they are protecting. They are also attached with a severity level. For example, Billing-Alter_line_item-Medium refer to a privilege for altering a bill's line-item in 'Billing' application module with a severity rating of 'medium'. Privileges are created and managed solely by the Application Designer. The names of Privileges are unique across all HMOS installation.

Privileges are grouped into 'Application Roles' (also called Privilege groups). In contrHAT to privileges, Application Roles are created to correspond to a business operation or a group of related business operations. The names of 'Application Roles' are unique only within an installation of HMOS, and has no meaning beyond the boundary of a single installation. The process of naming is always done by the HSA in consultation with all SDA's. The precise Separation of Concerns of a 'system meaning' of privileges and 'domain meaning' of application roles and the corresponding naming process and scheme is very suited for large enterprise security management.

SDA's can further group the Application Roles into Business Roles. Business Roles are the lowest assignment units to end-users of the system. Business Roles are made unique by the HMOS within each security domain and thus SDA can group the application roles to suit the domain needs unique to his or her domain and thus he was she is left free to create his own her on schemes of privilege administration. SDA's can also do cross-domain assignments. For example a pharmacy billing personnel in a 'pharmacy' may organizationally belong to 'finance' security domain, while can functionally be assigned a 'Browse Drugs List' application roles by Pharmacy SDA. Cross-domain assignments are, even though locally administered, are closely audited and can be restricted or fully prevented globally by HSA.

Any application in the AST of the HMOS should publish its securable resources. Lowest granular unit of items to be protected is called a 'Resource'. Resources can include 'actions' (which are logical operations or transactions performed by HMOS), fields (which are components in a user interface form) and objects (which are business objects or a group of business objects). Correspondingly HMOS offers action-level, field-level, object-level privileges.

The Publish—Subscribe Model of Communication

Figure 4:
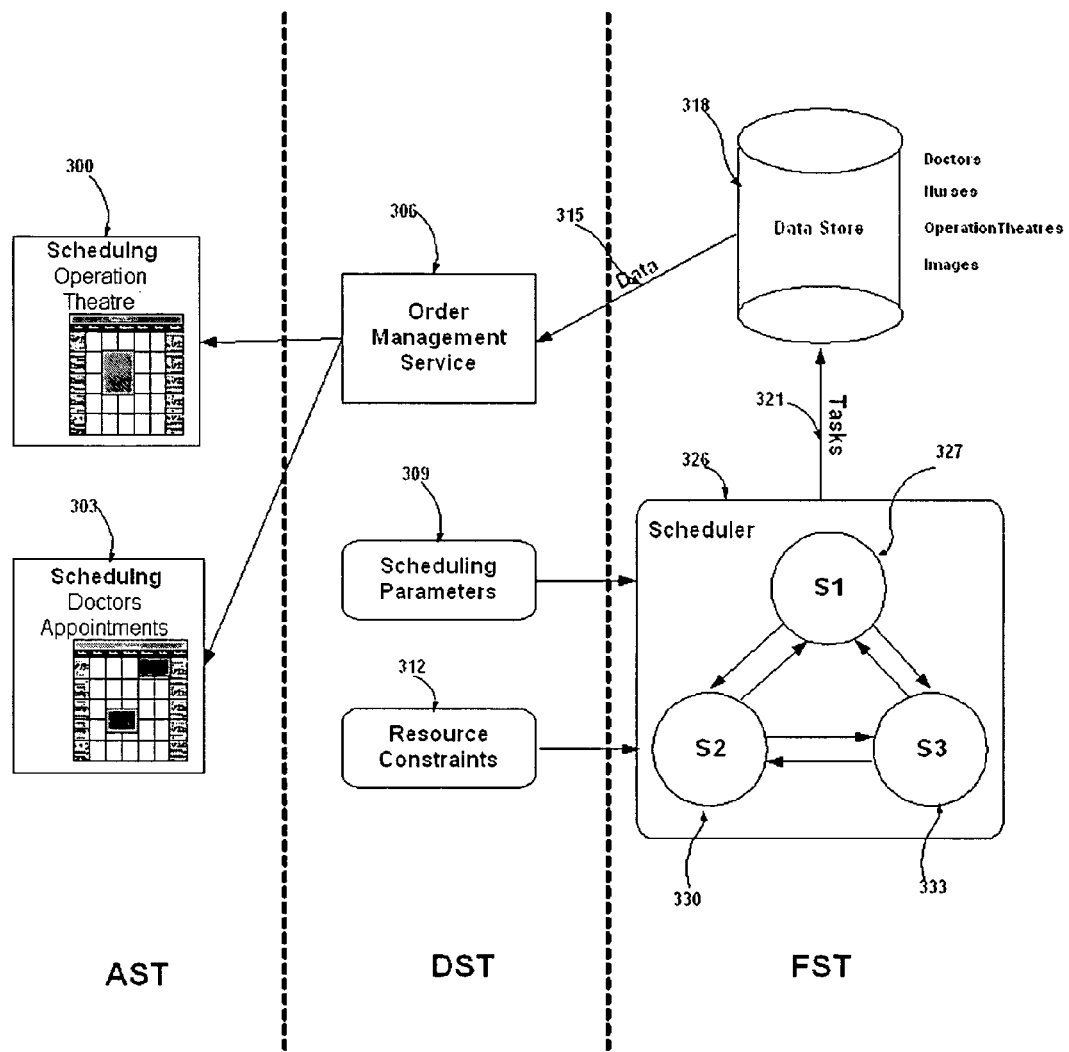

The Messaging Module of the Foundation Services is composed of an entity called Subscription Manager. The Messaging component uses the publish—subscribe model of communication. This forms the base of the platform-neutral nature of HMOS by which applications are isolated from environmental differences. The components of the subscription manager and its interaction with other HMOS components are depicted in FIG. 4. As shown in the figure, Subscription Manager (FIG. 10.603) is made up of a Message Publisher (FIG. 10.604), Message Manager (FIG. 10.605) and a Message Queue (FIG. 10.606) The Message Publisher is responsible for publishing the messages. Whenever a request for publishing a new message comes, the Message Publisher gets invoked. The Message Manager keeps track of the lifecycle of the messages and Meta information about the messages. The Message Queue is a priority-based queue of messages, which are yet to be subscribed. The priority of a message can be changed dynamically. The figure also shows a Message Store (FIG. 10.609). This is where all the messages are persisted for guaranteed message delivery. FIG. 10:600 represents the HMOS Application Services Tier, FIG. 10:602 the Domain Services Tier. FIG. 10: 607 shows the Active Subscribers, which can be any HMOS component.

Communication among various components of HMOS is achieved through the Publish—Subscribe Model in which components does not exchange events directly. Instead they directly or indirectly use the services of the Subscription Manager. The Subscription Manager propagates the event in the form of messages. Messaging can occur between components within a particular tier or across the tiers. It is also possible to target the message to components of a particular tier.

Almost all the components of HMOS directly or indirectly use the services of the Subscription Manager. Consider the example of the ADT module of the HIS, which belongs to the Application Tier of HMOS (FIG. 10.600) starting a workflow for the admission of the patient. The ADT module may use one or more than one components of the Domain Service Tier (FIG. 10.601). The task of raising a notification about admission request lies with the Workflow component of FST tier. For the accomplishment of the task the Workflow component will in turn use the services of the Subscription Manager. A message is published across all active subscribers (FIG. 10.607) from which the right subscriber responds to the message and initiates actions for completing the task. Subscription is achieved through the declaration of the components about the events in which it is interested. The publisher may or may not have to know about the identity of the subscriber. Likewise the subscriber need or need not be aware of the existence of the publisher. Message delivery is guaranteed in the sense that a permanent destination is set up for all outgoing messages and the response destination could be associated with an automatic persistent store. This message storage component is shown as FIG. 4.6. Also, the delivery of the message is in real time fashion so that if a message does not get subscribed within a time limit the system will raise a failure message to the appropriate component. Because the data can be sent from the publisher to the subscriber as soon as it becomes available, publish-subscribe architectures provide low latency delivery. This is very much needed since certain messages can be life critical. The same reason is applied for prioritizing the messages in the Message Queue (FIG. 10.606)

It is very costly to construct publications without prior knowledge of what subscribers are actually interested in. The subscription manager has a learning component by which it keeps track of the delivery of a message from a publisher. This helps in faster delivery of messages. The publisher also has the facility to specify criteria so that the messages are only delivered to the subscriber who matches the criteria. But in general, the flow of information from publishers to subscribers is determined by the specific interests of the subscribers rather than by any explicit subscriber criteria assigned by the publisher. With this communication pattern, subscribers subscribe to information with the subscription manager that is of interest to them without regard to any specific source, while publishers simply publish information without addressing it to any specific destination. The Subscription Manager is responsible for interpreting subscriptions and delivering the relevant publications to subscribers.

The Publish—Subscribe Model reduces the hardships of application development since the information does not need to be read or pulled; it is just made available simplifying tremendously the programming of communication in automation of tasks. Development of software modules for modality management can make use of this paradigm. For example, to read the data delivered by a particular modality it is only needed to create a subscriber for the particular event. Since events are simply a special form of message, HMOS explicitly support the development of event-oriented distributed applications ranging from user interfaces to server components.

Consider the real world scenario within a health care organization where a patient is ready for discharge as per the patient care management sub system (PCMS). Now this Information is published by PCMS through the Publish Manager component.

The Billing Sub System component of HIS has an active subscription with the Subscription Manager and identifies the message as a trigger and acts accordingly.

Application Service Tier

The following software modules resident within the HAL tier, enable it to carry out some of its prime responsibilities {such as, assuring user-transparent access, seamless integration with HMOS proprietary and third-party software packages}:

| Health Care Information System (HIS) |
|---|
| This software application in turn serves as the primary interface to the users in ADT, Billing and Ordercom domains as noted below. |
| ADT                Automated mechanisms for admission, discharge, and transfer of patients |
| Procurement Module     Purchase order creation and communication for both materials and drugs. |
| Electronic Medical Records Management Module (EMRS). |
| Patient Care Management Module (PCMS). |
| Authentication and authorization using smart cards and biometric devices. |
| Side effects of drugs, Interactions among drugs, and Interactions between drug and food interfaces with the database in Foundations Tier through the Domain Services Tier |
| Telemedicine for remote medical diagnosis and treatment with integrated video conferencing |
| ERP Systems            Electronic Resource Package |
| HR System               Human Resources System |
| Third-Party EMRs       Third-Party Electronic Medical Records |
| Finance Systems |

Admission, Discharge and Transfer

The software application module namely ADT which is part of the HIS of the Application tier using the API provided by Domain Services Tier includes the Admission of patients to the hospital, Transfer of patients between different kinds of rooms depending upon the procedures or services that has to be performed for the patient and Discharge of the patients from the hospital. The entire admission process can be considered as a set of smaller workflows and the process transaction manager should make sure that the integrity among the sub workflows are maintained The major admission workflow involves the sub workflows such as admission request from the out patient department, Financial agreements or counseling known as FIC, cash clearance/advance clearance known as admission clearance etc. The ADT module is accommodated with the facilities to request for a bed for the patient from any department or from the doctors assistant, getting the bed status of the entire hospital where by allocating appropriate bed to the patients and ordering drugs and other services to the patients from the corresponding nursing station or ward. The workflow environment provided along with the HMOS comprehensively advocates the request sending, bed allocation and the service ordering methods enabling the real time processing of each admission request and ordering requests. Those who are precisely authorized can pull out the details of the admitted patient at the different centers easily at any instance of time. The HMOS also has the ability to have the same function distributed among different centers where different functions are getting processed. The drug orders, other service orders, bed transfer requests and all related functions are integrated and the different instances of the functions are uniquely and accurately distributed.

The bed transfer for the patient is initiated when the concerned doctor is suggesting for some procedures (surgery for e.g.), which should be preformed in a different room or bed. The information about the room, the kind of bed, hours or days that the patient is allocating a particular kind of bed are matters very much under consideration and the HIS is furnished itself with a unique way by which the details of the bed transfers that the patient undergone are taken care off.

The discharge process mainly includes preparation of the final bill for the patients, which includes the calculation of bed charges and service charges. The bed charges are calculated based on the duration that the patient was allocated with a particular kind of bed. Once all orders are finished processing the final bill can be generated automatically against the orders and patient can be discharged once they clear their liabilities. The patient will also be given a Discharge Summary containing the results of all the diagnostics, procedures, medications and investigations done during his stay in the hospital.

Example Scenario Patient Admission Process

1: Legacy Systems

One of the most common and important process in any health care information system is the patient admission process. Patients who requires full time attention by a trained physician, those who are directed by the doctors to undergo certain procedures or services for some dates, and those who are going to undergo certain surgeries etc. has be admitted in the hospital. Whenever the doctor suggested that the patient has to admit for certain procedures, the actual admission process starts.

In the available legacy systems the capability of transferring concurrent knowledge across the different set of users is not that effective. So the process flow becomes very slow and tiresome. When the data is distributed across the network the transfer would still be slower and the data may not be the real time data.

The entire admission process can be considered as a set of smaller workflows and the process transaction manager should make sure that the integrity among the sub workflows are maintained. In the legacy systems it is cumbersome to maintain the list of complicated workflows, which will result in the slower velocity services to the patients.

The major admission workflow involves the sub workflows such as admission request from the out patient department, Financial agreements or counseling known as FIC, cash clearance/advance clearance known as admission clearance etc. All these will take time when we consider the fact that no real time information flow is happening. The patient or someone with the patient has to go to all different counters, sit and wait for hours and still they are not getting the necessary service that they want. These scenarios enlighten the thought to have workflow based messaging services across different sub processes. The HMOS is working on top of the above-mentioned concept, which is found to suits to the requirements as well as for the fully automated and timely processing of the services.

The fact that the legacy systems can not supply real time information in a distributed domain is overcome by the suitable supply of the messaging services across the domain. As the functional areas keep on increasing the distributed, domain specific data migration become too complex that the legacy system can't afford the performance degradation at the transactional areas. In a widely distributed domain like a health care middleware operating system the number of transaction as well as the criticality of the transactions will be higher to many other known domain and legacy systems find it difficult to manage these extremely difficult and complicated functionalities.

HMOS handles the complex domain specific information in an effective way. It has a message driven data transfer mechanism using which the user are supplied with the real time information whenever any change in any part of the data is affected and also he/she is the right user to review the change. Consider the case when the patient is coming for an admission. As soon as the patient is registered the user interface task list of the user who should know what to do next will be updated with the information that the patient has got registered and he/she will be coming to meet the doctor at any time. This information is vital as the concerned user can allocate a time slice of the doctor for that patient also and when the patient is coming there is no need of waiting for getting the doctor consultation as the every formalities of the consultation is already over as the user is provided with the information at the earliest time that one could imagine.

The user at the particular department will make an admission request as and when the doctor is suggested for admitting the patient for doing some procedure(s). The same admission request will pop up at the FIC administrators screen as a task item and all he/she has to do is give FIC clearance to the patient after having counseling. Since the states are related, after FIC clearance a message is published to the Admission such that a patient is ready for admission and the admission clerk can complete his/her task list as soon as possible. There is no case that the patient is waiting for getting the FIC clearance as a message is published for every state change. Hence the task list of the user is getting updated on every step so that the user will have a thorough Domain knowledge. Finally the duty of the staff reduces to, simply clearing their task list.

This kind of message driven service management across the users are the primary objective of the workflow implementation. This also explains how the workflow based, message driven, process and functional management helps in the faster distribution of domain specific information in a vast functional area like a hospital environment.

Purchase Management

Purchase Management Module (PMS) of HIS provides comprehensive coverage of the procurement functionality. PMS manages issuance of Purchase Orders (PO) for both disposable materials and drugs. The PMS Module, linked in close coordination with the Inventory and Financing modules, automates all aspects of an ordering process.

Purchase Item

Incorporation of the concept of a 'Purchase Item' by the PMS provides embellishments to the user-friendly aspects of HMOS based applications. Identified by designated part # a Purchase Item refers to an individual item within a PO. Purchase Item is central to creation of both a PO and Goods Received Note (GRN) in the PMS. Graphical definition of the Purchase Item' is illustrated below.

For every purchased item, is likely that multiple vendors can supply the same item. Furthermore, depending on the manufacturer, same vendor may have multiple catalog items that could alternately be used as equivalent to the item description. The 'Vendor-Manufacturer-Catalog Number' combination determines the uniqueness of a Purchase Item. A preferred vendor is one having the highest (pre-assigned) rating for each purchase item. The purchase item concept helps HMOS-users to select the most preferred vendor for each item to be procured before issuance of the PO.

Purchase Order Creation

The processes involved in the creation of a PO for both disposable material and drugs are similar. An approved Purchase Requisition (PRQ) shall exist prior to creation of the PO, which is then sent to the Purchase Manger for approval. Once the PO is approved, it is ready for release to the vendor/supplier. In case of any modifications to a PO, PMS will ensure that, only pre-authorized users can make any amendment. On receipt of the items against a specific PO, Goods Received Note (GRN) will be prepared. Stock updates within Inventory Management are performed only on confirmation of the Goods Received Note.

Automatic Conversion of Unit of Measure

PMS is endowed with a feature of automatic conversion of the vendor's standard units of measure to the hospital-standard unit of measure (UOM).

Purchase Order Reduction

This module has the ability to consolidate multiple purchase requests into a single PO. This provides a means to augment the procurement activity, by reducing the number of POs that need to be managed.

Partial Order Receiving

Partially delivered quantities—in a PO are managed by reducing the quantity in the purchase order. Un-delivered items can be identified as 'Pending' and the purchase order status will be held pending until complete delivery of all items.

Tracking Vendor and Manufacturer Performance

Purchase Management sub-system provides APIs to obtain comprehensive data on a vendor or manufacturer's performance. Offering different views of vendor and manufacturer activities also exposes multiple View Helper classes. For example, when multiple vendors supply the same purchase item, HMOS can provide statistical summary [tabular, graphical representation of data] of the item quantities supplied by each vendor over different time periods.

Electronic Medical Record Management Module

The increasing demand for well-structured and accessible patient data, in combination with developments in computer science, sparked a great interest in the development of an electronic patient record. HMOS worked on this direction and comes with a set of APIs for developing a comprehensive, confidential, interoperable, accessible, accountable, flexible Electronic Medical Record System in which data exchange will be according to public health care standards. And such systems will be able to accept data (historical, radiological, laboratory, etc) from multiple sources including physician's offices, hospital computer systems, laboratories, and patients' personal computers Public Standards Many current systems fragment medical records by using incompatible means of acquiring, processing, storing, and communicating data. These incompatibilities may result from a failure to recognize the need for interoperability or they may be deliberate, with the aim of locking consumers into using a particular system. Either way, the practice precludes sharing of data across different applications and institutions.

A notable feature of EMR module is instead of proprietary methods it uses open standards. At minimum, open standards allows exchange of information among different systems.

For example, HL7 (Health Level Seven) is a voluntary consensus standard for electronic data exchange in health care environments. It defines standard message formats for sending or receiving data on patient admissions, registration, discharge, or transfer; queries; orders; results; clinical observations; and billing. HMOS by using an open messaging standard such as HL7 allows different health applications, such as a laboratory system and a record system, to "talk" to each other.

Other standards have been adopted by HMOS for various other data exchanges: DICOM defines messages for encoding and exchanging medical images. Programs that exchange data according to open standards may nevertheless store and use those data internally in proprietary ways.

Comprehensiveness

Because care is normally provided to a patient by different doctors, nurses, pharmacists, and ancillary providers, and, with the passage of time, by different institutions in different geographical areas, each provider must be able to know what others are currently doing and what has previously been done. Outpatient records should contain, at least, problem lists, procedures, allergies, medications, immunizations, history of visits, family medical history, test results, doctors' and nursing notes, referral and discharge summaries, patient-provider communications, and patient directives. The records must also span a lifetime, so that a patient's medical and treatment history is available as a baseline and for retrospective analysis.

Accessibility

Medical records may be needed on a predictable basis (as at a scheduled doctor's visit) or on the spur of the moment (as in an emergency). They may be needed at a patient's usual place of care or far from home. They may be needed when the patient can consent to their use or when he or she is unconscious and only personal or societal policy can dictate use. Ideally, the records would be with the patient at all times, but alternatively they should be universally available, such as on the World Wide Web. In addition, with patients' permission, these records should be accessible to and usable by researchers and public health authorities.

Interoperability

Different computerized medical systems should be able to share records: they should be able to accept data (historical, radiological, laboratory, etc) from multiple sources, including doctors' offices, hospital computer systems, laboratories, and patients' personal computers. Without interoperability, even electronic medical records will remain fragmented. For different systems to share data effectively HMOS uses a common set of communication protocols and message formats and allow the import and export of all their data. By using common data structures and open source programming HMOS fosters the possibility of effective data exchange among systems.

Privacy and Confidentiality

For most patients, the appropriate degree of confidentiality will fall in between and will be a compromise between privacy and the desire to receive informed help from medical practitioners. Because an individual may have different preferences about different aspects of his or her medical history, access to various parts of the record should be authorized independently. For example, psychiatric notes may deserve closer protection than immunization history. Further, patients should be able to grant different access rights to different providers, based either on their role or on the particular individual. Most patients will probably also choose to provide a confidentiality "override" policy that would allow an authenticated health care provider in an emergency to gain access to records that he or she would not normally be able to, though at the cost of triggering an automatic audit. The EMR system that can build on HMOS can use the security and authorization features of HMOS, which can be easily integrated with it.

Accountability

Any access to or modification of a patient's record should be recorded and visible to the patient. Thus, data and judgments entered into the record must be identifiable by their source. Patients should be able to annotate and challenge interpretations in their records, though we believe they should not be able to delete or alter information entered by others. Patients should also be able to see who has accessed any parts of their record, under what circumstances, and for what purpose. Reliable authentication feature of HMOS is essential to make this feasible. Appropriate laws can reinforce accountability built into the records system.

Flexibility

Patients should be able to grant or deny study access to selected personal medical data. This can be based on personal policies or decisions about specific studies. An example policy might say that any study may use data if they will be stored only in aggregated, non-identifiable form. Whether patients are willing to be solicited on the basis of characteristics of their record should also be controllable. Patients could provide time limited keys to other parties to access a specified segment of their record. For example, they could permit hospitals to write to (but not read) the laboratory results section of their record. Or they could provide public health authorities with access to their immunization history. All these patient functions can be easily incorporated with the EMR system that is based on HMOS APIs Integrated Nursing Module The Integrated Nursing Module (IND) in AST provides designated users an option to bring up multiple views from various perspectives such as Nursing Station-wise view, Doctor-Specialty-wise view, and Ward-wise-view. HMOS system, armed by its sophisticated privilege control system, ensures that such viewing privileges and associated functionality are accessible only by pre-authorized users.

The IND module also provides HIS users a facility to designate a patient's clinical status to one of the following: 'Under IP Care', 'Marked for Discharge' etc. INS also furnishes a financial status entitled 'Send for Billing', which is a status-in-transition between clinical and financial status. These status transitions are processed under a strictly controlled rule base. IND provides facility to order material, drugs and services for patients. The bed transfer is efficiently tracked and will only be possible when all the orders are cleared and once the transfer is done the nursing station he previously occupied can do no order.

The IND application can be made available using the APIs provided by the Patient Care Management (PCM) module in the DST tier These APIs follow user-configurable rule-base. For instance, when a clinical status change needs to be processed, the PCM module calls on the services of 'View Helper' module within the FST tier to display the customized data corresponding for each view offered in the INS application.

Biometric Technology for Secure Access

A fingerprint offers a reliable and inexpensive means of authenticating an individual's identity; one far more secure than personal identification numbers (PINS) or passwords, which are subject to being compromised or forgotten. By linking the user directly to the transaction process through their fingerprint, proof is given that the authorized user is indeed present—not just someone who happens to know a short string of numbers or letters. This unique capability has been engineered into the HIS Biometric Authenticator, a complete, embeddable fingerprint identification system that can be inserted into a variety of access devices requiring user authentication. It performs all sensor, processor and decision-making functions within the module, greatly simplifying the incorporation of biometric recognition into small, mass-produced products such as smart cards.

The Technology

It employs a third generation capacitive array sensor chip that detects and captures small variations in finger surface capacitance and creates a three-dimensional electrical image of the fingerprint's unique pattern. To enroll a user in the Biometric Authenticator fingerprint identification system, one or more fingerprints of the authorized person must first be registered. This is accomplished in conjunction with an external enrollment station that activates and controls the process. First the user places his/her fingertip on the Biometric Authenticator module's sensor. It detects and captures the small variations in finger surface-capacitance and creates a three-dimensional electrical image of the fingerprint's unique papillary pattern. These signals are verified and then programmed under the control of the enrollment station into protected memory on the module. Upon completion of the enrollment process the module is "locked" and subsequent placement of any finger on the sensor triggers the verification process. This involves comparing the previously stored "registered" template with the fingerprint image using a special programmed algorithm. In the case of a fingerprint-enabled smartcard, if the result matches, the person holding the card (not just someone who happens to know the PIN) is verified as its authorized user.

Drug Interactions and Drug-Diet Interactions

Adverse Drug Reactions (ADR) and drug allergies can cause serious threat to the life of patients. Identification of drugs that are known to cause ADRs can avoid prescription of drugs that may cause an allergic reaction in patients. This intelligence has been built into the Ordercom sub system of HIS so that the drug ordering process will automatically go through a screening process that checks whether the prescribed drug can cause negative side effects to the patient. Additionally, if cross-sensitivities of drugs that are pharmacologically or chemically related to the patient's primary allergens are found then the system will raise proper alerts. This is achieved through maintaining the patient's drug and clinical history and by the usage of the drug information data store provided by the HMOS Foundation Services Tier. The doctor also has the provision to go through the specific allergens that are known to the patient so that he can avoid prescribing drugs that can generate adverse effects with the patients.

Dietary consistency is the key to maintaining a sustained, stable response during illness. Certain food items should be avoided for the proper functioning of some drug items.

Scenario 1: Legacy Systems

A typical case study i.e. the patient dietary can be taken for explaining how the rule based health care information system helps in the better functionality of the entire process. If we consider the case of legacy systems where there is no tracking of concurrent information, it will make the process a mess, which can result in the major functional failure in the entire workflow and some times lead to inefficient patient care.

In legacy systems there is no way to keep the information about the interaction between drugs and diet . . . . Here all the process should work according to manual instructions. i.e. the some way the doctor himself or the nursing assistant should inform the dietary system about the permissible food details. Most of the time the decision taking here is not based on medical history of the patient or any knowledge base. There is no way by which the nursing assistant will immediately able to know what diet will fit to the current prescription and this can be ended up in supplying contradictory diet to a patient.

So most of the times, lack of right information at the right time leads to unhealthy condition of the Patients.

Scenario 2: HIS on HMOS

This type of severe mistakes can be avoided in a rule based health care management system, which will be having all information about diet and the drug discrepancies. It also supplied with a set of functional rules, which can be used to quickly get the details from a knowledge base of the diet that should be supplied to the patient if his/her prescription includes a particular kind of medicine. The rules can be edited and supplied on time and the entire workflow will be changing according to the rule. This case is seemingly small but functionally hard on which the rule can be applied and rule is effective in all such cases where there should take some decisions based up on some predefined criteria.

This type of severe mistakes can be avoided in a rule based health care management system, which will be having all information about diet and the drug discrepancies. So in HIS as soon as the doctor prescribes the medicine a message composed of a list of permissible food items is published to the dietary system. The message is formed on the basis of predefined rules that are taken from the knowledge base for drug-food, drug-allergy, medical records and medical history for that patient.

It is also supplied with a set of functional rules, which can be used to quickly get the details from a knowledge base of the diet that should be supplied to the patient if his/her prescription includes a particular kind of medicine. The rules can be edited and supplied on time and the entire workflow will be changing according to the rule. This can be an assurance given to the patient by the health care organization that within their system patient care is done as much as possible.

Telemedicine and Integrated Video Conferencing

The domain service DICOM API and PACS facility enables the HMOS to act as a Service Class Provider so that all the clients connected with the HMOS application are enriched by the images. If a satellite pinging facility to the remote machines in another hospital, it is easy to integrate and retrieve the remote images to the PACS server of HMOS.

Here the HMOS Domain Service Tier APIs does the handshaking for establishing the communication. After getting connection it can either query for an image or send an image through the network. The two machines, the local and remote, work as if they are in the same local area network.

Quality of Service (QoS)

HMOS is geared to pursue a simple yet organized approach to facilitate monitoring and control of health care business processes, in an efficient and cost-effective manner. Given the multi-dimensional nature in usage of products like HMOS, encompassing a wide range of functional domains, different QoS parameters are of interest, relevant to the user's perspective. Design of HMOS incorporates measures to guarantee a minimum level of QoS across all functional domains. QoS issues addressed within HMOS include:

| Functional Domain | Measure of Performance |
| --- | --- |
| User Interface/ Screen Navigation | human-factors based screen access/control Context sensitive help Context sensitive error tracking/ Automatic error report generation |
| multiple simultaneous HMOS users | Connectivity latency Guaranteed bandwidth Minimum transaction response time High Availability/low down-time Self-alert/correction of illegal field values screen by Screen |
| Financial Performance' Asset Management | Return on Investment Accuracy and validated |
| Technical Performance Software Upgrades | Error-control/fault-tolerant Non-disruptive/NSA |

The clinical data is integrated, secured and authenticated in accordance with the HIPAA compliant rules. Not only that the HMOS also provides an environment where those application which can go par with the HIPAA rule only be run on top of HMOS. This provides integration at the different level of the application and providing a standardized way of developing applications, which can run using HMOS as a platform.

Horizontal and Vertical Extensibility of HMOS

As newer standards emerge, they too can be incorporated into these tiers, thus ensuring horizontal expandability. This technology enables users to choose the 'best of breed' products from different suppliers, and to optimize the price/performance ratio and quality of their information systems. Such a federation strategy allows users to make the best use of existing products and to replace or add components in accordance with their needs.

HMOS provide plug and play architecture i.e. it is adaptable to change. Consider the case where a new protocol or a new standard is introduced in the field of health care. Since HMOS is horizontally expandable it is easy to plug the new service without affecting the core structure or the top-level applications.

Both FST and DST tiers of HMOS are horizontally extensible. Newer services can be added to either of these tiers. For example to ensure that all applications written on HMOS support a new health care standard, the new standard can added as a Service in DST. By virtue of this, all HMOS applications are ensured compliancy to this standard. Vertical extensibility of HMOS means that health care applications may be developed above an existing set of applications in the AST.

HMOS provides a common base and technology to build health care and hospital information systems locally in accordance with the specific needs of users. Handling of objects, invoking of services and therefore providing adequate interfaces are the objectives of middleware services of HMOS. It enables communication and co-operation of application systems from different vendors on different platforms and with different application environments. In some hospitals legacy systems need to be preserved to protect past investments and to guarantee continuity of operations. This is made possible by the utilization of HMOS services which allows easy migration from existing solutions towards an open, distributed information system at moderate costs.

The openness and modularity, and resulting flexibility of HMOS based systems facilitate easy adaptation to organization changes, both at short and long term, and allow effective use of technologies for business processes. In this respect the middleware-based open, architectural framework could be used as the change agent. Moreover, through open, standardized interfaces of HMOS services, health care organizations can realize even more savings downstream due to lower cost, interoperable solutions.

By integrating the management of all the low level technical tasks in to a HMOS, we are achieving the same benefits as a systems programmer achieves from low-level operating systems like Windows or Unix. The functional modules of FST and DST together provide the essential services needed to build and manage an enterprise level Hospital Information System. HMOS provides FST and DST tiers of services and a set of services and tools in Application Service Tier (AST) that makes writing extensible and customizable applications is easy. HMOS effectively manages the resources for the efficient functioning of modules in the Application Services Tier and controls the interaction between the functional entities by scheduling of the core services.

It will be apparent to the skilled artisan that the system of the invention described above in several embodiments is much more broadly applicable than to the narrow field of health care services. The examples of health care services are an important application, but serve as examples only. The characteristics of the invention can be applied in any area of human endeavor where distributed tasks must be planned and scheduled, and existing data must be sought and applied. Such areas include information management of all sorts, manufacturing systems, design systems for both hardware and software, and much more.

Further it will be apparent to the skilled artisan that there are a variety of ways that the functionality described might be implemented within the spirit and scope of the invention. There may be more or fewer modules, for example, and it is notoriously well known that different programmers may provide the same or similar functionality with very different code in different order. For these and other reasons the invention should be accorded the scope of the claims that follow.

The invention claimed is:

1. A system for developing health care business applications, comprising:
    a server coupled to a data repository;
    a software system executing on the server from a non-transitory machine-readable physical medium, the software system comprising:
    a foundation services tier (FST) providing modules with operating system functionalities including resource allocation and a scheduling function, and modules with middleware functionalities including messaging and knowledge integration, wherein all tasks that are scheduled are initiated through the scheduler function, with each defined task comprising constraints, and if the constraints cannot be satisfied within a current context, the scheduler notifies a task initiator with a precise indication of the reasons, providing Quality of Service (QoS) guarantees, and wherein user's security authorizations are managed by a Globally-Controlled Locally Managed (GCLM) system in which users are grouped into non-overlapping security domains, each managed by a security domain administrator (SDA), and users are assigned privileges defined by application designers at a lowest level of granularity;
    a domain services tier (DST) comprising a workflow software (SW) engine having specific process states, and thus having state transitions, triggered by events, all defined by an XML-based configuration mechanism of the workflow software engine, and Application Programming Interfaces (APIs) for developing the healthcare business process applications, wherein each call to an API is routed to a Quality of Service (QoS) subsystem before being executed, and QoS standards are enforced in operation of the API and any healthcare business process application implemented through the API, and wherein the healthcare business process applications are developed for a specific healthcare enterprise, and after development are deployed to be executed at the specific enterprise by users who are associated with and granted privileges for that enterprise; and
    an application services tier (AST) comprising specific healthcare business process applications developed using the workflow software engine and APIs of the DST, the healthcare business process applications implemented using services of the workflow software engine and communicating with one another in the AST using a publish-subscribe model provided by a subscription manager, in which messages are published by individual applications without being addressed to any specific destination, and applications subscribe according to interest without regard to any specific source, and wherein in the AST all entered data is routed through a health care standards subsystem before being accepted as clinical data, thus ensuring standards compliance.

2. The system of claim 1 wherein the healthcare business process applications include applications for admission of a patient to a healthcare facility, discharge of a patient from a health care facility, transfer of a patient within a healthcare facility, billing a patient for services provided.

3. The system of claim 1 wherein the healthcare business process applications include an Integrated Nursing Module (IND) providing users options to view information from various perspectives, including a Nursing Station-wise view, a Doctor-Specialty-wise view, and Ward-wise-view.

4. The system of claim 3 wherein views are limited to pre-authorized users.

5. The system of claim 3 wherein users are provided facility to designate a patient's clinical status to one or more of 'Under IP Care', 'Marked for Discharge', and 'Send for Billing'.

* * * * *